(12) United States Patent
Thiele

(10) Patent No.: US 12,000,846 B2
(45) Date of Patent: Jun. 4, 2024

(54) CLICK-MASS SPECTROMETRY OF ALKYNE-LABELED COMPOUNDS

(71) Applicant: Rheinische Friedrich-Wilhelms-Universitaet Bonn, Bonn (DE)

(72) Inventor: Christoph Thiele, Bonn (DE)

(73) Assignee: Rheinische Friedrich-Wilhelms-Universitaet Bonn, Bonn (DE)

( * ) Notice: Subject to any disclaimer, the term of this patent is extended or adjusted under 35 U.S.C. 154(b) by 654 days.

(21) Appl. No.: 17/254,922

(22) PCT Filed: Jun. 28, 2019

(86) PCT No.: PCT/EP2019/067398
§ 371 (c)(1),
(2) Date: Dec. 22, 2020

(87) PCT Pub. No.: WO2020/002634
PCT Pub. Date: Jan. 2, 2020

(65) Prior Publication Data
US 2021/0270856 A1    Sep. 2, 2021

(30) Foreign Application Priority Data
Jun. 28, 2018 (EP) .................................. 18180525

(51) Int. Cl.
*G01N 33/92* (2006.01)
*C07C 247/04* (2006.01)
(Continued)

(52) U.S. Cl.
CPC ........... *G01N 33/92* (2013.01); *C07C 247/04* (2013.01); *C07D 249/04* (2013.01);
(Continued)

(58) Field of Classification Search
CPC ................ G01N 33/92; G01N 1/4022; G01N 2001/4027; G01N 2458/15;
(Continued)

(56) References Cited

U.S. PATENT DOCUMENTS

2014/0018318 A1\* 1/2014 Cravatt .................. C07F 5/022
548/110
2019/0125882 A1\* 5/2019 Ogle .................... C07D 265/26

FOREIGN PATENT DOCUMENTS

CN      103983764 A  \*  8/2014  ............ G01N 33/58
WO      2011036059 A1    3/2011
(Continued)

OTHER PUBLICATIONS

Berry et al., "Oxidative Esterification of Aldehydes Using Mesoionic 1,2,3-Triazolyl Carbene Organocatalysts", 2014, American Chemical Society, 16, 3676-3679. (Year: 2014).\*
(Continued)

*Primary Examiner* — Jennifer Wecker
*Assistant Examiner* — Kathryn Elizabeth Limbaugh
(74) *Attorney, Agent, or Firm* — Rimon PC

(57) ABSTRACT

Nitrogen containing compounds may have formulas (I), (II) and (IV), and such compounds may be suitable for detecting alkyne group containing organic compounds by mass spectrometry. Furthermore, methods may also include synthesizing these compounds, detecting of organic compounds containing the specific compounds, uses of the compounds in mass spectrometry for determining enzyme activity or monitoring the lipid metabolism in a cell, and a kit which contains at least one of these compounds and at least one internal standard.

16 Claims, 7 Drawing Sheets

(51) Int. Cl.
 *C07D 249/04* (2006.01)
 *C07D 487/04* (2006.01)
 *G01N 1/40* (2006.01)

(52) U.S. Cl.
 CPC ......... *C07D 487/04* (2013.01); *G01N 1/4022* (2013.01); *C07B 2200/05* (2013.01); *G01N 2001/4027* (2013.01); *G01N 2458/15* (2013.01); *G01N 2560/00* (2013.01); *G01N 2570/00* (2013.01)

(58) Field of Classification Search
 CPC ............ G01N 2560/00; G01N 2570/00; C07C 247/04; C07D 249/04; C07D 487/04; C07B 2200/05
 See application file for complete search history.

(56) References Cited

FOREIGN PATENT DOCUMENTS

| WO | 2013105118 A1 | 7/2013 | |
|---|---|---|---|
| WO | WO-2014001527 A2 * | 1/2014 | ........... C07C 215/24 |
| WO | 2017040762 A2 | 3/2017 | |

OTHER PUBLICATIONS

Thiele et al., "Tracing Fatty Acid Metabolism by Click Chemistry", ACS Chemical Biology, 2012, pp. 2004-2011, American Chemical Society.

Rillahan et al., "On-Chip Synthesis and Screening of a Sialoside Library Yields a High Affinity Ligand for Siglec-7", ACS Chemical Biology, 2013, pp. 1417-1422, American Chemical Society.

Database Caplus [Online], Database accession No. 2012:934688, 2012, Chemical Abstracts Service, Columbus, Ohio, US.

Engler et al., "Effects of Side Group Functionality and Molecular Weight on the Activity of Synthetic Antimicrobial Polypeptides", Biomacromolecules, 2011, pp. 1666-1674, American Chemical Society.

Rudolf et al., "Copper-Assisted Click Reactions for Activity-Based Proteomics: Fine-Tuned Ligands and Refined Conditions Extend the Scope of Application", ChemBioChem, 2013, pp. 2447-2455, Wiley-VCH Verlag GmbH & Co. KGaA, Weinheim, DE.

Jao et al., "Biosynthetic Labeling and Two-Color Imaging of Phospholipids in Cells", ChemBioChem, 2015, pp. 472-476, Wiley-VCH Verlag GmbH & Co. KGaA, Weinheim, DE.

Shaya et al., "Turn-on Fluorene Push-Pull Probes with High Brightness and Photostability for Visualizing Lipid Order in Biomembranes", ACS Chemical Biology, 2017, pp. 3022-3030, American Chemical Society.

Liu et al., "GSH-Responsive supramolecular nanoparticles constructed by β-D-galactose-modified pillar[5]arene and camptothecin prodrug for targeted anticancer drug delivery", Chemical Communications, 2017, pp. 8596-8599, The Royal Society of Chemistry.

Liu et al., "Dual-Responsive Bola-Type Supra-Amphiphile Constructed from Water-Soluble Pillar[5]arene and Naphthalimide-Containing Amphiphile for Intracellular Drug Delivery", ACS Applied Materials & Interfaces, 2017, pp. 4843-4850, American Chemical Society.

Extended European search report from parallel European Patent Application 18 180 525.0 dated Jan. 18, 2019, 10 pages (for reference purposes only).

International search report from parallel PCT Patent Application PCT/EP2019/067398 dated Sep. 26, 2019, 16 pages (for reference purposes only).

Examination report dated Jun. 29, 2023, received for parallel European patent application No. 19 733 070.7, 6 pages (reference purpose only).

Soriano Del Amo et al., "Biocompatible Copper(I) Catalysts for in Vivo Imaging of Glycans", J. Am. Chem. Soc., 2010, pp. 16893-16899, vol. 132, American Chemical Society.

\* cited by examiner

CLICK-MASS SPECTROMETRY OF ALKYNE-LABELED COMPOUNDS

CROSS-REFERENCE TO RELATED APPLICATIONS

The present application is a national stage entry according to 35 U.S.C. § 371 of PCT application No.: PCT/EP2019/067398 filed on Jun. 28, 2019; which claims priority to European Patent Application Serial No.: 18180525.0 filed on Jun. 28, 2018; all of which are incorporated herein by reference in their entirety and for all purposes.

TECHNICAL FIELD

The present invention relates to specific nitrogen containing compounds of formulas (I), (II) and (IV), which are suitable to be used in a method to detect alkyne group containing organic compounds by mass spectrometry. Furthermore, the present invention relates to methods for the synthesis of these compounds and for the detection of organic compounds containing the specific compounds, uses of the compounds in mass spectrometry, for determining enzyme activity or monitoring the lipid metabolism in a cell, and a kit, which contains at least one of these compounds and at least one internal standard.

BACKGROUND

The metabolism of lipids, especially of fatty acids or sterols, is in the focus of current research, since it can help to understand and detect diseases such as metabolic syndrome or type 2 diabetes. For studying the lipid metabolism, it is common that labeled precursor substances are administered to a test system, in which they can be introduced into newly synthetized lipids. Different types of labeling are known in the art, which require different types of analysis methods. Well-known labels are radioisotopes (such as $^3$H or $^{14}$C), stable isotopes (such as $^2$H, $^{13}$C) or fluorescence labels (e.g. fluorescent lipids). Up to know, the lipid metabolism is mostly monitored by methods using radioactive tracer. Furthermore, alkyne-labeling of organic compounds with subsequent detection by fluorescence is a known method (Thiele et al. ACS Chem. Biol. 7, 2012).

All these known methods have one or more disadvantages, such as long analysis times in the range of several days, only low to moderate sensitivity (need of high sample concentrations) or resolution (no suitable detection of lipid species, only lipid classes), complex analysis methods or complex sample preparation before analysis. For example, radioisotopes, fluorescent lipids and alkyne-labeled lipids, detected by fluorescence enable only the measurement of lipid classes (e.g. all phosphatidylcholines, all triacylglycerols), but they cannot measure lipid species in a suitable way (e.g. phosphatidylcholines or triacylglycerols with certain fatty acid combinations). Furthermore, radioisotope and stable isotope methods require high amounts of sample concentrations (>20 pmol) for exact measurements.

Therefore, there is a demand for new labeling and analysis methods, which overcome one or more of these disadvantages.

SUMMARY

The inventors thus had the object to provide compounds suitable as detection system for a new, short and simple method to monitor, analyze and measure organic compounds, preferably organic compounds of the lipid metabolism, with high sensitivity and resolution, without the utilization of radioactive tracers.

Surprisingly, the inventors found that the above-stated object can be solved by one of the following compounds, or the uses, methods, and kit associated therewith:

In a first aspect, a compound may have formula (I)

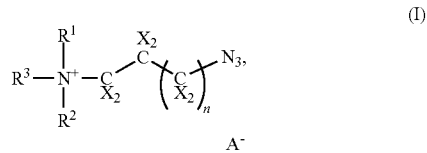

wherein $R^1$ to $R^3$ are independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl, whereby the linear, branched alkyl or cycloalkyl groups can contain one or more -D and/or one or more $^{13}$C carbon atoms; or wherein $R^1$ is a free valence and $R^2$ and $R^3$ form a 4 to 7-membered cyclic hydrocarbon ring, which can contain one or more -D and/or one or more $^{13}$C carbon atoms;

wherein n is 1 to 4;

wherein each X is independently selected from —H, -D, —F, —$^{19}$F, —OH, —OD;

$A^-$ is an anion;

wherein each N in the compound can independently be $^{15}$N, and wherein each C in the compound can independently be $^{13}$C.

In a second aspect, a compound may have formula (II)

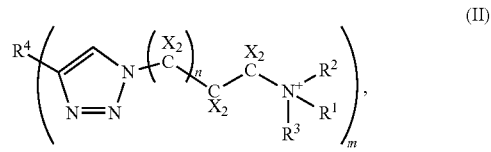

wherein X, $R^1$ to $R^3$ and n are defined as in aspect 1, wherein m is 1 or 2 or 3, wherein each N in the compound can independently be $^{15}$N, and wherein each C in the compound can independently be $^{13}$C, obtained by reacting a compound of formula (I) with an organic compound of formula (III)

wherein $R^4$ is derived from an organic compound, and wherein m is 1 or 2 or 3.

In a third aspect, a compound may have formula (IV)

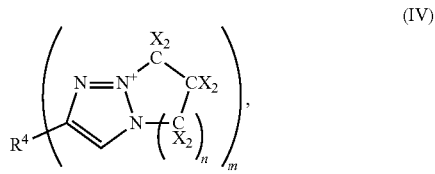

wherein $R^4$, X, m and n are defined as in aspect 2, wherein each N in the compound can independently be $^{15}N$, and wherein each C in the compound can independently be $^{13}C$, which is obtainable by treating a compound of formula (II) in a mass spectrometer.

In a fourth aspect, the invention relates to the use of a compound in mass spectrometry.

In a fifth aspect, the invention relates to the use of a compound for determining an enzyme activity.

In a sixth aspect, the invention relates to the use of a compound for analyzing or monitoring the lipid metabolism in a cell.

In a seventh aspect, a method may detect an organic compound by:
a) reacting in a solvent at least one compound of formula (III) with at least one compound of formula (I) in the presence of catalytic amounts of Cu(I) to form a compound of formula (II);
b) optionally purifying the compound of formula (II) by chromatography or liquid-liquid extraction; and
c) detecting the compound of formula (II) and/or formula (IV).

In an eighth aspect, a compound of formula (I) may be produced, wherein
a compound according to formula (V)

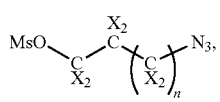
(V)

wherein X is independently selected from —H, -D, —F, —$^{19}F$, —OH, —OD;
n is 1 to 4;
Ms is a leaving group, preferably mesylate;
wherein each N in the compound can independently be $^{15}N$, and wherein each C in the compound can independently be $^{13}C$;
1a) is reacted with $NR^1R^2R^3$,
wherein $R^1$, $R^2$ and $R^3$ are independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl, whereby the linear, branched alkyl or cycloalkyl groups can contain one or more -D and/or one or more $^{13}C$ carbon atoms, or wherein $R^1$ is a free valence and $R^2$ and $R^3$ form a 4 to 7-membered cyclic hydrocarbon ring, which can contain one or more -D and/or one or more $^{13}C$ carbon atoms; wherein each N can independently be $^{15}N$ and wherein each C can independently be $^{13}C$; in an organic solvent to give the compound according to formula (I) or
1b) a compound according to formula (V) as defined above is
reacted with $NR^1R^3H$, wherein
$R^1$ and $R^3$ are independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl, whereby the linear, branched alkyl or cycloalkyl groups can contain one or more -D and/or one or more $^{13}C$ carbon atoms, or wherein $R^1$ and $R^3$ form a 4 to 7-membered cyclic hydrocarbon ring, which can contain one or more -D and/or one or more $^{13}C$ carbon atoms; and wherein N can independently be $^{15}N$; in an organic solvent to give a compound according to formula (VI)

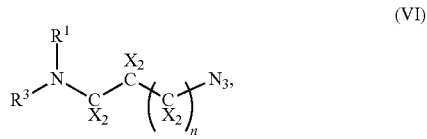
(VI)

wherein X, $R^1$ and $R^3$ are as defined above; wherein each N in the compound can independently be $^{15}N$ and wherein each C in the compound can independently be $^{13}C$; and wherein the compound of formula (VI), if $R^1$ and $R^3$ are not a 4 to 7-membered cyclic hydrocarbon ring is subsequently reacted with $R^2Y$, wherein
$R^2$ is independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl, whereby the linear, branched alkyl or cycloalkyl group can contain one or more -D and/or one or more $^{13}C$ carbon atoms; and
—Y is a halogen group;
to give the compound according to formula (I).

Finally, in a ninth aspect, a kit may be used for the detection of alkyne-labeled compounds, comprising or consisting of
i) at least one compound according to formula (I); and
ii) at least one internal standard of alkyne-labeled compounds according to formula (III).

The present compounds for a highly efficient and fast detection method on the basis of alkyne-labeled precursors. The alkyne-labeled precursors according to formula (III) react with organic compounds according to formula (I), and the resulting compounds of formula (II) can be directly analyzed by mass spectrometry. Preferably, a maximum resolution and sensitivity occur. In addition, the analysis time (click reaction and subsequent mass spectrometry) is shorter compared to known methods, and is preferably in the range of hours. Furthermore, the compounds of formula (I) as well as the resulting compounds of formula (II) after click reaction and after fragmentation by mass spectrometry (compounds of formula (IV)) surprisingly show a high stability and are easy to handle. In an improved and preferred method, multiplexing of samples can be carried out.

The terms "one or more" or "at least one", as interchangeably used herein, relate to at least one, or at least 2, 3, 4, 5, 6, 7, 8, 9, 10, 11, 12, 13, 14, 15, 20, 25 or a plurality of e.g. compounds. In this connection, the term "plurality" means more than one, preferably 2-1000, more preferably 2-100, even more preferably 2-50, still more preferably 2-25 and most preferably 2-20. In view of "at least one" compound, the type of a compound and not on the absolute amount of a compound is referred to.

Numeric values specified without decimal places here refer to the full value specified with one decimal place, i.e. for example, 99% means 99.0%, unless otherwise defined.

The terms "about" or "approximately", in connection with a numerical value, refers to a variance of ±10% with respect to the given numerical value. For example, "about 8% intensity" means the range of 7.2 to 8.8% of intensity.

If a compound is described to be substituted, the substituents are generally known to the skilled person. Substituents can be selected from -D, —F, —$^{19}F$, —Cl, —Br, —I, —OH, —OD, =O, —$OR^1$, —$NH_2$, —NHR$^1$, —NR$^1_2$, and —COOR$^1$, more preferred from -D, —F, —$^{19}$F, —OH and —OD, wherein R$^1$ is an alkyl group having 1 to 20 carbon atoms.

The feature "organic compounds" refers to hydrocarbon containing compounds, which are preferably lipids, nucleic acids, amino acids, peptides or proteins.

Embodiments, features, and advantages become apparent to the person skilled in the following detailed description and claims. Each feature from one embodiment can be used in any other embodiment. Furthermore, the examples contained herein are intended to describe and illustrate the invention, but do not restrict it. In particular, the invention is not limited to these examples.

The following abbreviations are used within this application:

AcCl=acetyl chloride, CE=cholesterol ester, Cer=ceramide, CL=cardiolipin, Click-Palmitate=16-heptadecynoic acid, DAG=diacylglycerol, DG=diglyceride, DGAT=diacylglycerol-O-acyltransferase, DGAT1=diacylglycerol-O-acyltransferase 1, DGAT2=diacylglycerol-O-acyltransferase 2, DHP=dihydropyran, DMEA=N,N-dimethyl-N-ethylamine, DMF=dimethylformamide, EDC/DMAP=3-(ethyliminomethyleneamino)-N,N-dimethylpropan-1-amine/4-dimethylaminopyridine, FA=fatty acid, HESI=heated electrospray ionization, HPLC=high performance liquid chromatography, LC=liquid chromatography, LPC=lysophosphatidylcholine, MAG=monoacylglycerol, MEA=N-methyl-N-ethylamine, MeOH=methanol, MFQL=molecular fragment query language, MG=monoglyceride, Ms=mesylate, MS=mass spectrometry, MS1=primary mass spectrum without fragmentation, MS2=secondary fragment spectrum in tandem mass spectrometry, MS/MS=secondary fragment spectrum in tandem mass spectrometry, NHS=N-hydroxysuccinimide ester, NMR=nuclear magnetic resonance spectroscopy, NL=neutral loss, PA=phosphatidic acid, PC=phosphatidylcholine, PCC=pyridinium chlorochromate, PE=phosphatidylethanolamine, PG=phosphatidylglycerol, PI=phosphatidylinositol, PS=phosphatidylserine, SMART=Simplified Method—Applied Radial Technology, sn=stereospecific numbering, SPE=solid phase extraction, TAG=triacylglycerol, TG=triglyceride, THF=tetrahydrofuran, THP=tetrahydropyran, TLC=thin layer chromatography.

According to the first aspect (referred to as item 1 as well), the compound of formula (I) is claimed

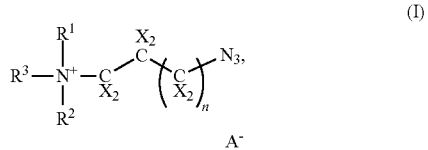

(I)

wherein R$^1$ to R$^3$ are independently selected from substituted or unsubstituted linear C$_1$-C$_{10}$ alkyl, substituted or unsubstituted branched C$_3$-C$_{10}$ alkyl, substituted or unsubstituted C$_3$-C$_{10}$ cycloalkyl, whereby the linear, branched alkyl or cycloalkyl groups can contain one or more -D and/or one or more $^{13}$C carbon atoms; or wherein R$^1$ is a free valence and R$^2$ and R$^3$ form a 4 to 7-membered cyclic hydrocarbon ring, which can contain one or more -D and/or one or more $^{13}$C carbon atoms; wherein each N in the compound can independently be $^{15}$N, preferably 0, 1, 2, 3 or 4 N are $^{15}$N, and wherein each C in the compound can independently be $^{13}$C.

In a preferred embodiment, R$^1$ to R$^3$ are independently selected from substituted or unsubstituted linear C$_1$-C$_{10}$ alkyl, preferably selected from substituted or unsubstituted linear C$_1$-C$_3$ alkyl, whereby the linear alkyl groups can contain one or more -D and/or one or more $^{13}$C carbon atoms.

Preferably, when R$^1$ and R$^2$ are both —CH$_3$, R$^3$ is not —CH$_3$, more preferably R$^3$ is —CH$_2$CH$_3$. This embodiment avoids the elimination of a trimethylamine leaving group during mass spectrometry. Trimethylamine is a compound, which can naturally occur in samples, for example from choline and its derivatives, in particular from phosphatidylcholine. The elimination of trimethylamine should in some cases be avoided. It is therefore particularly preferred, if R$^1$ and R$^2$ are both —CH$_3$, and R$^3$ is —CH$_2$CH$_3$. Then, N-ethyl-N,N-dimethylamine is the leaving group.

In one embodiment, R$^1$ is a free valence and R$^2$ and R$^3$ form a 4 to 7-membered hydrocarbon cyclic ring, preferably R$^2$ and R$^3$ form a 5-membered cyclic ring, most preferably a tetrahydropyrrol ring. The cyclic ring can contain one or more -D and/or one or more $^{13}$C carbon atoms.

In a non-limiting embodiment, n is 1 to 4, preferably n is 1, 2 or 3, more preferably n is 2.

In a non-limiting embodiment, X is independently selected from —H, -D, —F, —$^{19}$F, —OH, —OD, preferably X is —H or -D, more preferably 1 to 4 -D are present and the remaining X are —H.

In one preferred embodiment all X are —H.

In a non-limiting embodiment, A$^-$ is an anion. In a preferred embodiment, A$^-$ is preferably selected from salts of carbon acids, like formate, acetate, propionate; halogenates like PF$_6^-$; halites; halides, like F$^-$, Cl$^-$, Br$^-$, I$^-$; oxides; perchlorates like ClO$_4^-$; sulfides; sulfates; phosphates; borates; fluoro borates like BF$_4^-$; thionates; mesylate, i.e. CH$_3$SO$_3^-$; imides; amides; nitrides; nitrates; cyanides; cyanates; carboxylates; carbonates or mixtures thereof; more preferably from formate, acetate, propionate, halides, mesylate, BF$_4^-$, PF$_6^-$, ClO$_4^-$ or mixtures thereof, most preferably BF$_4^-$.

In a non-limiting embodiment, each N in the compound can independently be $^{15}$N, preferably 0, 1, 2, 3 or 4 N are $^{15}$N; most preferably 0 N are $^{15}$N. Furthermore, each C in the compound can independently be $^{13}$C, preferably 0 or 1 $^{13}$C are present.

In a preferred embodiment, R$^1$ to R$^3$ are independently selected from substituted or unsubstituted linear C$_1$-C$_3$ alkyl, whereby the linear alkyl groups can contain one or more -D and/or one or more $^{13}$C carbon atoms, preferably 0 to 1 $^{13}$C carbon atoms are contained in all linear alkyl groups R$^1$ to R$^3$ in sum;

n is 1, 2 or 3, preferably n is 2;

X is independently selected from —H or -D, more preferably 1 to 4 -D are present and the remaining X are —H or all X are —H.

Preferably, if one or more groups of R$^1$ to R$^3$ are substituted, the substituent is independently selected from -D, —F, —$^{19}$F, —OH, OD, in particular -D, more preferably 1 to 4 substituents, in particular -D, are present.

In one embodiment according to formula (I), the compound is of formula (VII)

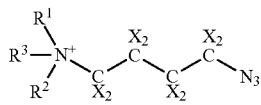

(VII)

wherein $R^1$ to $R^3$ are independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl, whereby the linear, branched alkyl or cycloalkyl groups can contain one or more -D and/or one or more $^{13}C$ carbon atoms; or wherein $R^1$ is a free valence and $R^2$ and $R^3$ form a 4 to 7-membered cyclic hydrocarbon ring, which can contain one or more -D and/or one or more $^{13}C$ carbon atoms;

preferably wherein $R^1$ to $R^3$ are independently selected from substituted or unsubstituted linear $C_1$-$C_{10}$ alkyl, more preferably selected from substituted or unsubstituted linear $C_1$-$C_3$ alkyl, most preferably $R^1$ is a methyl group, $R^2$ is a methyl group and $R^3$ is an ethyl group, wherein $R^1$ to $R^3$ can contain one or more -D and/or one or more $^{13}C$ carbon atoms; and/or wherein X is independently selected from —H, -D, —F, —$^{19}$F, —OH, —OD, more preferably each X is independently selected from —H or -D, most preferably 1 to 4 -D are present and the remaining X are —H or all X are —H; and/or wherein $A^-$ is an anion, selected from salts of carbon acids, like formate, acetate, propionate; halogenates like $PF_6^-$; halites; halides, like $F^-$, $Cl^-$, $Br^-$, $I^-$; oxides; perchlorates like $ClO_4^-$; sulfides; sulfates; phosphates; borates; fluoro borates like $BF_4^-$; thionates; mesylate, i.e. $CH_3SO_3^-$; imides; amides; nitrides; nitrates; cyanides; cyanates; carboxylates; carbonates or mixtures thereof; more preferably from formate, acetate, propionate, halides, mesylate, $BF_4^-$, $PF_6^-$, $ClO_4^-$ or mixtures thereof, most preferably $BF_4^-$; and wherein each N in the compound can independently be $^{15}N$, preferably 0, 1, 2, 3 or 4 N are $^{15}N$, more preferably 0 N in the compound are $^{15}N$ and/or wherein each C in the compound can be independently $^{13}C$, more preferably 0 or 1 $^{13}C$ is present.

In one preferred embodiment according to formula (I), the compound is of formula (VIII)

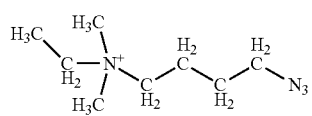

(VIII)

wherein $A^-$ is an anion, preferably selected from salts of carbon acids, like formate, acetate, propionate; halogenates like $PF_6^-$; halites; halides, like $F^-$, $Cl^-$, $Br^-$, $I^-$; oxides; perchlorates like $ClO_4^-$; sulfides; sulfates; phosphates; borates; fluoro borates like $BF_4^-$ thionates; mesylate, i.e. $CH_3SO_3^-$; imides; amides; nitrides; nitrates; cyanides; cyanates; carboxylates; carbonates or mixtures thereof; more preferably from formate, acetate, propionate, halides, mesylate, $BF_4^-$, $PF_6^-$, $ClO_4^-$ or mixtures thereof, most preferably $BF_4^-$.

The compound of formula (VIII) is referred to as C171 as well.

In another preferred embodiment according to formula (I), the compound is of formula (IX)

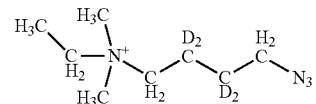

(IX)

wherein $A^-$ is an anion, preferably selected from salts of carbon acids, like formate, acetate, propionate; halogenates like $PF_6^-$; halites; halides, like $F^-$, $Cl^-$, $Br^-$, $I^-$; oxides; perchlorates like $ClO_4^-$; sulfides; sulfates; phosphates; borates; fluoro borates like $BF_4^-$; thionates; mesylate, i.e. $CH_3SO_3^-$; imides; amides; nitrides; nitrates; cyanides; cyanates; carboxylates; carbonates or mixtures thereof; more preferably from formate, acetate, propionate, halides, mesylate, $BF_4^-$, $PF_6^-$, $ClO_4^-$ or mixtures thereof, most preferably $BF_4^-$.

The compound of formula (IX) is referred to as C175-73 as well.

Preferably, the deuterized substituents -D of the butyl chain can be integrated into the molecule by reacting butyrolactone with sodium borodeuteride, according to the chemical synthesis shown in FIG. 2.

In another preferred embodiment according to formula (I), the compound is one of formulae (X) to (XIII)

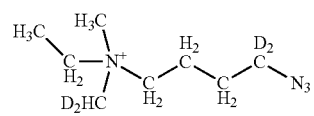

(X)

or

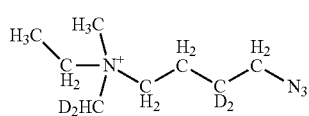

(XI)

or

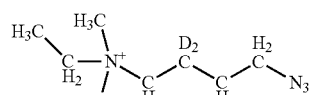

(XII)

or

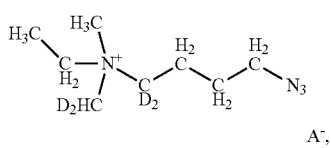

(XIII)

wherein A⁻ is an anion, preferably selected from salts of carbon acids, like formate, acetate, propionate; halogenates like $PF_6^-$; halites; halides, like $F^-$, $Cl^-$, $Br^-$, $I^-$; oxides; perchlorates like $ClO_4^-$; sulfides; sulfates; phosphates; borates; fluoro borates like $BF_4^-$; thionates; mesylate, i.e. $CH_3SO_3^-$; imides; amides; nitrides; nitrates; cyanides; cyanates; carboxylates; carbonates or mixtures thereof; more preferably from formate, acetate, propionate, halides, mesylate, $BF_4^-$, $PF_6^-$, $ClO_4^-$ or mixtures thereof, most preferably $BF_4^-$.

The compounds of formulae (X) to (XIII) are isomers of C175-75.

In another preferred embodiment according to formula (I), the compound is of formula (XIV)

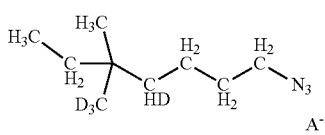

(XIV)

wherein A⁻ is an anion, preferably selected from salts of carbon acids, like formate, acetate, propionate; halogenates like $PF_6^-$; halites; halides, like $F^-$, $Cl^-$, $Br^-$, $I^-$; oxides; perchlorates like $ClO_4^-$; sulfides; sulfates; phosphates; borates; fluoro borates like $BF_4^-$; thionates; mesylate, i.e. $CH_3SO_3^-$; imides; amides; nitrides; nitrates; cyanides; cyanates; carboxylates; carbonates or mixtures thereof; more preferably from formate, acetate, propionate, halides, mesylate, $BF_4^-$, $PF_6^-$, $ClO_4^-$ or mixtures thereof, most preferably $BF_4^-$.

The compound of formula (XIV) is referred to as C175-76 as well.

In another preferred embodiment according to formula (I), the compound is of formula (XV)

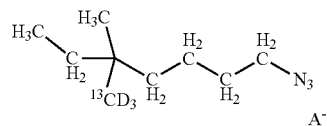

(XV)

wherein A⁻ is an anion, preferably selected from salts of carbon acids, like formate, acetate, propionate; halogenates like $PF_6^-$; halites; halides, like $F^-$, $Cl^-$, $Br^-$, $I^-$; oxides; perchlorates like $ClO_4^-$; sulfides; sulfates; phosphates; borates; fluoro borates like $BF_4^-$; thionates; mesylate, i.e. $CH_3SO_3^-$; imides; amides; nitrides; nitrates; cyanides; cyanates; carboxylates; carbonates or mixtures thereof; more preferably from formate, acetate, propionate, halides, mesylate, $BF_4^-$, $PF_6^-$, $ClO_4^-$ or mixtures thereof, most preferably $BF_4^-$.

The compound of formula (XV) is referred to as C175-77 as well.

In a preferred embodiment, the compound of formula (I) is selected from the group of compounds of formula (VIII) to (XV) or mixtures thereof.

In one embodiment, each N of the compounds of formula (VII) can independently be $^{15}N$, preferably 0, 1, 2, 3 or 4 N are $^{15}N$, most preferably, 0 N are $^{15}N$.

In one embodiment, each N of the compounds of formula (VIII) to (XV) can independently be $^{15}N$, preferably 0, 1, 2, 3 or 4 N are $^{15}N$, most preferably, 0 N are $^{15}N$.

The heavy isotopes —$^{13}C$ and -D can be introduced into the groups $R^1$ to $R^3$ of compounds of formula (I) by converting compound (V) with $HNR^1R^3$(dialkyl amine) in an organic solvent to give the compound according to formula (VI), wherein $R^1$ and $R^3$ are independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl, whereby the linear, branched alkyl or cycloalkyl groups can contain one or more -D and/or one or more $^{13}C$ carbon atoms; and wherein N can be $^{15}N$;

wherein the compound of formula (VI) can subsequently react with $R^2Y$ to give compounds of formula (I) (see FIG. 2).

In this embodiment, $R^2$ is independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl, whereby the linear, branched alkyl or cycloalkyl group can contain one or more -D and/or one or more $^{13}C$ carbon atoms; and —Y is a halogen group, preferably —F, —Cl, —Br, or —I, more preferred —Br or —I, most preferred —I.

The applied organic solvent for the chemical synthesis of compounds of formula (I) according to item 1 can be every suitable organic solvent, which is known to the person skilled in the art, for example the organic solvent can be dimethylformamide, acetonitrile, trimethylamine, methanol, ethanol, 1-propanol, 2-propanol, dimethylsulfoxide, dichloromethane, or tetrahydrofuran.

According to the second aspect (also referred to as item 2), a compound of formula (II) is claimed

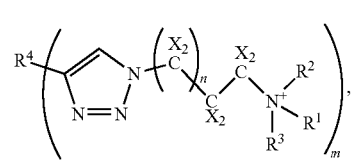

(II)

wherein X, $R^1$ to $R^3$ and n are defined as in item 1, wherein m is 1 or 2 or 3, preferably 1 or 2, more preferably 1, wherein each N in the compound can independently be $^{15}N$, preferably 0, 1, 2, 3 or 4 N are $^{15}N$, and wherein each C in the compound can independently be $^{13}C$, obtained by reacting a compound of formula (I) according to item 1 with an organic compound of formula (III)

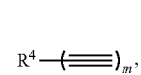

(III)

wherein $R^4$ is derived from an organic compound, preferably derived from lipids, nucleic acids, amino acids, peptides or proteins, more preferably from lipids selected from the group consisting of fatty acids, such as oleate and palmitate, and ester, amide, hydroxyl or keto derivatives thereof, sterol esters, cholesterol, cholesterol esters, cardiolipins, phosphatidylcholines, phosphatidylethanolamines, phosphatidylglycerols, phosphatidylinositols, phosphatidylserines, mono-, di-, triacylglycerols, ceramides, sphingosines and sphinganins, wherein m is 1 or 2 or 3, preferably 1 or 2, more preferably 1.

The term "derived from an organic compound" with regard to $R^4$ means that up to three alkyne groups, preferably one or two, more preferably one alkyne group, replace(s) respectively an H atom of the organic compound to form the compound of formula (III). The organic compound, before being substituted with the up to three alkyne groups, is, in preferred embodiments, selected from lipids, nucleic acids, amino acids, peptides or proteins. In further preferred embodiments, the organic compound, before being substituted with the up to three alkyne groups, is selected from fatty acids, including but not limited to $C_8$-$C_{22}$ fatty acids, such as oleate, myristate, laurate, palmitate, stearate, and ester, amide, hydroxyl or keto derivatives thereof, sterol esters, cholesterol, cholesterol esters, cardiolipins, phosphatidylcholines, phosphatidylethanolamines, phosphatidylglycerols, phosphatidylinositols, phosphatidylserines, mono-, di-, triacylglycerols, ceramides, sphingosines and sphinganins.

Furthermore, since the before-mentioned compounds, in particular alkyne-labeled fatty acids can be added to a test system, e.g. to a cell, tissue, organ, whole organism or biological fluid, and then can be integrated into higher lipids by metabolism, the resulting alkyne-labeled compounds obtained after the metabolic process, i.e. typically the higher lipids thus generated, are considered to be within the definition of the compound of formula (III). In various embodiments, one or two or three different alkyne-labeled fatty acids according to formula (III) are integrated in a lipid, which is thereby alkyne-labeled as well and consequently has 1 or 2 or 3 group(s) derived from the alkyne-labeled fatty acid(s). The lipids thus generated may include those listed above, such as sterol esters, cholesterol, cholesterol esters, cardiolipins, phosphatidylcholines, phosphatidylethanolamines, phosphatidylglycerols, phosphatidylinositols, phosphatidylserines, mono-, di-, triacylglycerols, ceramides, sphingosines and sphinganins.

In various non-limiting embodiments, $R^4$, comprises one or more D (deuterium) and/or one or more $^{13}C$ carbon atoms, preferably 1 or 2 or 3 or 4 or 5 or 6 or 7 or 8 or 9 or 10 or more D, preferably 8 D and/or 1 or 2 or 3 or 4 or 5 or 6 or 7 or 8 or 9 or 10 or more $^{13}C$ carbon atoms, preferably >6 $^{13}C$ carbon atoms, more preferably 8 or 9 or 10 $^{13}C$ carbon atoms, most preferably 9 $^{13}C$. Preferably, $R^4$ comprises either one or more D or one or more $^{13}C$ carbon atoms as defined above. It is understood that the D atoms replace H atoms and the $^{13}C$ atoms replace $^{12}C$ atoms in the otherwise identical molecules.

Methods for the integration of $^{13}C$ atoms and/or D atoms into compounds are common in the state of the art and known to the skilled person. For example, one suitable method is described for Pentadec-11c-enoic acid (12,13,14,15-D8, FA15:1-D8) in the example section, without being limited to this method.

In various embodiments, the organic compound according to formula (III) comprises a single alkyne group (m=1). Preferably, the alkyne group is linked to a fatty acid comprised in the $R^4$ group. Typically, this fatty acid may be an even or uneven (odd), saturated or unsaturated fatty acid.

In various embodiments, the compound according to formula (III) is a free fatty acid linked to an alkyne group. This compound can, for example, be added to a test system to be integrated in a lipid. In these embodiments, the resulting compound, which is according to formula (III) as well, comprises in its $R^4$ group a group derived from the fatty acid, which is linked to the alkyne group. In a non-limiting embodiment, if a free fatty acid linked to an alkyne group is integrated in a lipid, the at least one fatty acid group is referred to as "fatty acid" as well.

Generally, the linkage of the $R^4$ moiety or group to the alkyne group may occur via a terminal C atom of the compound from which $R^4$ is derived, such as a lipid. For example, this means that if $R^4$ is derived from palmitic acid, the alkyne group may be coupled to the C atom in the 16 position. This similarly applies to all compounds that comprise long alkyl or alkenyl chains. This linkage may be such that the alkyne group replaces an H atom in the organic compound.

The term "even fatty acid" refers, for example without being limited to those, to fatty acids with 8 or 10 or 12 or 14 or 16 or 18 or 20 or 22 C atoms, wherein one or more C atoms may be substituted by $^{13}C$ carbon atoms.

The term "uneven fatty acid" refers, for example without being limited to those, to fatty acids with 9 or 11 or 13 or 15 or 17 or 19 or 21 or 23 C atoms, wherein one or more C atoms may be substituted by $^{13}C$ atoms.

The term "saturated fatty acid" typically refers to fatty acids, which do not comprise one or more double bonds within the carbon chain.

The term "unsaturated fatty acid" typically refers to fatty acids, which comprise one or more double bonds within the carbon chain, e.g. monounsaturated fatty acids, or polyunsaturated fatty acids comprising at least 2 double bonds within the carbon chain (e.g. 1 or 2 or 3 or 4 or 6 C=C double bonds).

In some embodiments, the fatty acid may comprise 1 or 2 or 3 or 4 or 5 or 6 or 7 or 8 or 9 or 10 or more $^{13}C$ carbon atoms, preferably >6 $^{13}C$ carbon atoms, more preferably 8 or 9 or 10 $^{13}C$ carbon atoms, most preferably 9 $^{13}C$ carbon atoms. One non-limiting example of such a fatty acid is FA 16:2-$^{13}C9$, which can be linked to an alkyne group and thus forms a compound according to formula (III), which is preferred. The term FA 16:2-$^{13}C9$ refers to a twofold unsaturated fatty acid with 16 C atoms, wherein 9 of the C atoms are substituted by $^{13}C$ atoms.

In various non-limiting embodiments, the organic compound according to formula (III) comprises 2 alkyne groups (m=2) which are linked to different carbon atoms of the $R^4$ group. Preferably, if more than one fatty acid is present in the organic compound, one alkyne group is linked to one fatty acid comprised in the $R^4$ group and the other alkyne group is linked to a second fatty acid comprised in the $R^4$ group. In this embodiment, $R^4$ is preferably derived from lipids, more preferably from di- or triacylglycerol (DAG or TAG). Typically, the comprised fatty acids may be independently selected from even or uneven, saturated or unsaturated fatty acids. In some embodiments, at least one of the fatty acids comprises 1 or 2 or 3 or 4 or 5 or 6 or 7 or 8 or 9 or 10 or more $^{13}C$ carbon atoms preferably >6 $^{13}C$ carbon atoms, more preferably 8 or 9 or 10 $^{13}C$ carbon atoms, e.g. at least one fatty acid is FA 16:2-$^{13}C9$, which is linked to an alkyne group.

In various non-limiting embodiments, the organic compound according to formula (III) comprises 1 or 2 alkyne groups as defined above. In this embodiment, the $R^4$ group may further comprise a deuterium-labeled fatty acid, wherein this fatty acid is preferably not linked to one of the alkyne groups. Preferably, said fatty acid comprises one or more D, more preferably 1 or 2 or 3 or 4 or 5 or 6 or 7 or 8 or 9 or 10 or more D, most preferably 8 D atoms. Preferably, the $R^4$ group is derived from a lipid, more preferably from diacylglycerol, if one alkyne group is comprised in the compound of formula (III) or triacylglycerol if two alkyne groups are comprised in the compound of formula (III). For example, the deuterium labeled fatty acid comprised in the $R^4$ group may be FA 15:1-d8. The term FA 15:1-d8 refers to a monounsaturated fatty acid with 15 C atoms, wherein 8 of the H atoms are substituted by D atoms. Preferably, these embodiments of the organic compound according to formula (III) are applied in the internal standard mixture described below, more preferably, the internal standard mixture comprises organic compounds according to formula (III) comprising 1 and/or 2 alkyne-groups, wherein the compounds further comprise a deuterium-labeled fatty acid as described above.

In various non-limiting embodiments, the organic compound according to formula (III) comprises 3 alkyne groups (m=3) which are linked to different carbon atoms of the $R^4$ group. Preferably, if more than one fatty acid is present in the organic compound, one alkyne group is linked to one fatty acid comprised in the $R^4$ group, the second alkyne group is linked to a second fatty acid comprised in the $R^4$ group and the third alkyne group is linked to a third fatty acid comprised in the $R^4$ group. In this embodiment, $R^4$ is preferably derived from lipids, more preferably from triacylglycerol (TAG). Typically, these fatty acids may be independently selected from even or uneven, saturated or unsaturated fatty acids. In some embodiments, at least one of the fatty acids comprises 1 or 2 or 3 or 4 or 5 or 6 or 7 or 8 or 9 or 10 or more $^{13}C$ carbon atoms preferably >6 $^{13}C$ carbon atoms, more preferably 8 or 9 or 10 $^{13}C$ carbon atoms, e.g. at least one fatty acid is FA 16:2-$^{13}C9$ which is linked to an alkyne group.

In a non-limiting embodiment, the reaction between compounds of formula (I) according to item 1 and compounds of formula (III) according to item 2 is referred to as "click-reaction". Preferably, the click reagent of formula (I) reacts with alkyne-labeled organic compounds, preferably lipids, of formula (III) to produce a compound according to formula (II) (see•FIG. 1).

After the click-reaction, the compound according to formula (II) may comprise 1 or 2 or 3 of the following groups, depending on the value of m in formula (III):

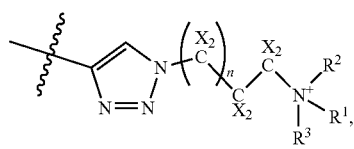

wherein X, $R^1$ to $R^3$ and n are defined as in item 1.

For example, if the compound of formula (III) comprises one alkyne group (m=1), the compound of formula (II) comprises one group of

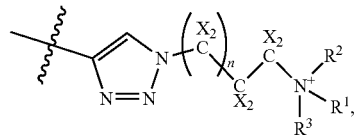

which is linked to $R^4$, preferably to one fatty acid group of $R^4$.

For example, if the compound of formula (III) comprises two alkyne groups (m=2), the compound of formula (II) comprises two groups of

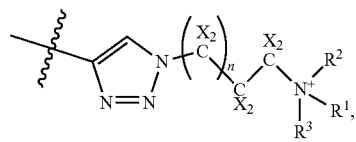

which are preferably linked to different carbon atoms of $R^4$, more preferably to two different fatty acid groups of $R^4$.

For example, if the compound of formula (III) comprises three alkyne groups (m=3), the compound of formula (II) comprises three groups of

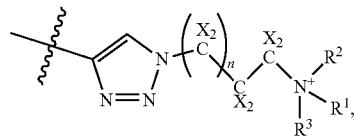

which are preferably linked to different carbon atoms of $R^4$, more preferably to three different fatty acid groups of $R^4$.

The $R^4$ group of the compound of formula (II) is derived from an organic compound, preferably derived from lipids, nucleic acids, amino acids, peptides or proteins, more preferably from lipids selected from the group consisting of fatty acids like oleate, palmitate, and ester, amide, hydroxyl or keto derivatives thereof, sterol ester, cholesterol, cholesterol ester, cardiolipin, phosphatidylcholine, phosphatidylethanolamine, phosphatidylglycerol, phosphatidylinositol, phosphatidylserine, mono-, di-, triacylglycerol, ceramide, sphingosine and sphinganine. In various non-limiting embodiments, $R^4$ comprises one or more D and/or one or more $^{13}C$ carbon atoms, preferably 1 or 2 or 3 or 4 or 5 or 6 or 7 or 8 or 9 or 10 or more D, preferably 8 D atoms and/or 1 or 2 or 3 or 4 or 5 or 6 or 7 or 8 or 9 or 10 or more $^{13}C$ carbon atoms, preferably >6 $^{13}C$ carbon atoms, more preferably 8 or 9 or 10 $^{13}C$ carbon atoms. Preferably, $R^4$ which is derived from an organic compound as defined above comprises either one or more D or one or more $^{13}C$ carbon atoms.

The click reagents contain three basic units:
1. an azido group —$N_3$, which enables the click reaction with the alkyne;
2. a hydrocarbon chain, preferably a propyl, butyl or pentyl chain, more preferred a butyl chain, which can work as a spacer; and
3. preferably a trialkylammonium group;
wherein each part of the click reagent may contain $^{13}C$, $^{15}N$ and/or -D atoms.

Most preferably within this application, the click reagents are C171 and C175-73, -75, -76 and -77. The group of C175-73, -75, -76, and -77 is referred to as C175-XX as well.

Click reagents can further contain heavy isotopes such as -D, $^{19}$F, —OD, $^{15}$N or $^{13}$C. The preferred click reagent C171 does not contain any isotopic labels, but the preferred reagents of C175-XX contain 1 to 4 -D and 0 to 1 $^{13}$C carbon atoms in the molecule (see FIG. 5).

In a non-limiting embodiment, the compound of formula (I) contains an anion $A^-$. Preferably, the anion $A^-$ is selected from salts of carbon acids, like formate, acetate, propionate; halogenates like $PF_6^-$; halites; halides, like $F^-$, $Cl^-$, $Br^-$, $I^-$; oxides; perchlorates like $ClO_4^-$; sulfides; sulfates; phosphates; borates; fluoro borates like $BF_4^-$; thionates; mesylate, i.e. $CH_3SO_3^-$; imides; amides; nitrides; nitrates; cyanides; cyanates; carboxylates; carbonates or mixtures thereof; more preferably from formate, acetate, propionate, halides, mesylate, $BF_4^-$, $PF_6^-$, $ClO_4^-$ or mixtures thereof, most preferably $BF_4^-$.

The click reagent in combination with $BF_4^-$ shows a good solubility in water and alcohols.

After click reaction for the formation of compounds of formula (II), the anion $A^-$ is still present in the reaction mixture, as it is dissolved in the reaction mixture or in the organic solvent. A removal of the counter ion after click reaction by suitable purification steps is possible.

The compounds of formulae (I) to (IV) can be detected by a mass spectrometer.

The compound according to formula (IV) may comprise 1 or 2 or 3 of the following groups:

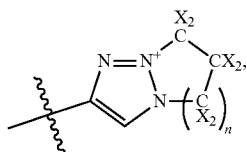

wherein X and n are defined as in item 3, depending on the number of

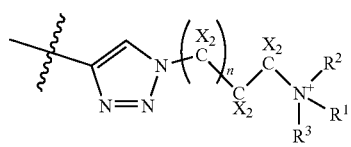

groups of formula (II), in the following referred to as unit A.

For example, if the compound of formula (II) comprises one unit A, the compound of formula (IV) comprises one group of

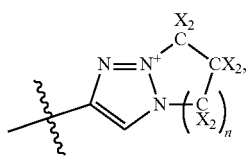

which is linked to $R^4$, preferably to one fatty acid group of $R^4$.

For example, if the compound of formula (II) comprises two units A, the compound of formula (IV) comprises two groups of

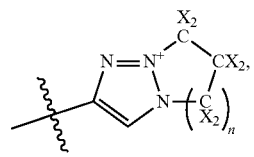

which are preferably linked to different carbon atoms of $R^4$, preferably to two different fatty acid groups of $R^4$.

For example, if the compound of formula (II) comprises three units A, the compound of formula (IV) comprises three groups of

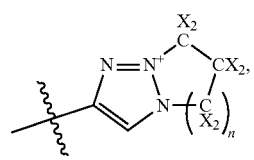

which are preferably linked to different carbon atoms of $R^4$, preferably to three different fatty acid groups of $R^4$.

The $R^4$ group of the compound of formula (IV) is derived from an organic compound, preferably derived from lipids, nucleic acids, amino acids, peptides or proteins, more preferably from lipids selected from the group consisting of fatty acids like oleate, palmitate, and ester, amide, hydroxyl or keto derivatives thereof, sterol ester, cholesterol, cholesterol ester, cardiolipin, phosphatidylcholine, phosphatidylethanolamine, phosphatidylglycerol, phosphatidylinositol, phosphatidylserine, mono-, di-, triacylglycerol, ceramide, sphingosine and sphinganine. In various non-limiting embodiments, $R^4$ comprises one or more D and/or one or more $^{13}$C carbon atoms, preferably 1 or 2 or 3 or 4 or 5 or 6 or 7 or 8 or 9 or 10 or more D, preferably 8 D atoms and/or 1 or 2 or 3 or 4 or 5 or 6 or 7 or 8 or 9 or 10 or more $^{13}$C carbon atoms, preferably >6 $^{13}$C carbon atoms, more preferably 8 or 9 or 10 $^{13}$C carbon atoms. Preferably, $R^4$ which is derived from an organic compound as defined above comprises either one or more D or one or more $^{13}$C carbon atoms as defined above.

In preferred embodiments, the mass spectrometer is a tandem mass spectrometer.

Furthermore, in preferred embodiments, the compounds of formula (I), (II) and (IV) can be used to determine enzyme activities in test systems, for example in bacteria, archaea, fungi, yeast, plants, animals, mammals or humans, preferably in mammals or humans.

Therefore, alkyne-labeled organic compounds according to formula (III) can be added or injected to a test system. These alkyne-labeled substances will be used in the metabolism of the test system.

Preferably, the alkyne-labeled organic compound of formula (III) is derived from a lipid, a nucleic acid, an amino acid, a peptide or a protein, more preferably a lipid selected from the group consisting of fatty acids like oleate, palmitate, and ester, amide, hydroxyl or keto derivatives thereof, sterol ester, cholesterol, cholesterol ester, cardiolipin, phosphatidylcholine, phosphatidylethanolamine, phosphatidylglycerol, phosphatidylinositol, phosphatidylserine, mono-, di-, triacylglycerol, ceramide, sphingosine and sphinganine.

Preferably, determined enzyme activities are activities of enzymes active in the lipid metabolism of the test system. For example, the activity of dehydrogenases, hydratases, thiolases, acyltransferases and many more, known to the person skilled.

In a preferred embodiment, the compounds of formula (I), (II) and (IV) can be used to analyse or monitor the lipid metabolism in a cell.

For example, alkyne-labeled fatty acids, which are according to formula (III) can be added to a test system, which can be integrated into higher lipids in the lipid metabolism, which form thereby alkyne-labeled organic compounds according to formula (III) as well, derived from the alkyne-labeled fatty acids.

In the following an alkyne-labeled fatty acid according to formula (III) is referred to as "alkyne-labeled fatty acid" as well.

In various non-limiting embodiments, at least one alkyne-labeled fatty acid, preferably at least two alkyne-labeled fatty acids, more preferably at least three alkyne-labeled fatty acids are added to said test system, preferably to a cell, a tissue, an organ, a whole organism or a biological fluid. Preferably, the fatty acids are selected from even or uneven, saturated or unsaturated alkyne-labeled fatty acids, which may comprise 1 or 2 or 3 or 4 or 5 or 6 or 7 or 8 or 9 or 10 or more $^{13}C$ carbon atoms, preferably >6 $^{13}C$ carbon atoms, more preferably 8 or 9 or 10 $^{13}C$ carbon atoms, most preferably 9 $^{13}C$ carbon atoms. In case fatty acids comprise $^{13}C$ atoms, they are termed as $^{13}C$-(carbon atom-)labeled. In one embodiment, the first fatty acid is an even, saturated or unsaturated, preferably unsaturated, alkyne-labeled fatty acid and the second fatty acid is an uneven, saturated or unsaturated, preferably unsaturated, alkyne-labeled fatty acid or vice versa. In another embodiment, one or both, preferably one, of the fatty acids described above comprise 1 or 2 or 3 or 4 or 5 or 6 or 7 or 8 or 9 or 10 or more $^{13}C$ carbon atoms, preferably >6 $^{13}C$ carbon atoms, more preferably 8 or 9 or 10 $^{13}C$ carbon atoms, most preferably 9 $^{13}C$ carbon atoms, e.g. the even fatty acid is FA 16:2-$^{13}C9$, which is linked to an alkyne group.

In another embodiment, the first fatty acid is an even, saturated or unsaturated, preferably unsaturated, alkyne-labeled fatty acid, the second fatty acid is an uneven, saturated or unsaturated, preferably unsaturated, alkyne-labeled fatty acid, and the third fatty acid is an even or uneven, saturated or unsaturated, preferably unsaturated, alkyne-labeled fatty acid comprising 1 or 2 or 3 or 4 or 5 or 6 or 7 or 8 or 9 or 10 or more $^{13}C$ carbon atoms, preferably >6 $^{13}C$ carbon atoms, more preferably 8 or 9 or 10 $^{13}C$ carbon atoms, most preferably 9 $^{13}C$ carbon atoms, e.g. FA 16:2-$^{13}C9$, which is linked to an alkyne group.

In various non-limiting embodiments, one or more of the fatty acids described above may comprise 1 or 2 or 3 or 4 or 5 or 6 or 7 or 8 or 9 or 10 or more deuterium atoms (D), preferably 8 D. In case fatty acids comprise deuterium atoms, they are named as deuterium (D)-labeled. However, it is not preferred, that the at least one alkyne-labeled fatty acid comprises one or more D atoms, in particular not if one or more $^{13}C$ atoms are comprised.

Preferably, the fatty acids described above are integrated into higher lipids in the lipid metabolism, which are thereby alkyne-labeled and/or deuterium-labeled and/or $^{13}C$-labeled as well, according to the compound of formula (III). Afterwards, these compounds according to formula (III) can be used, preferably after separating and/or purifying the compounds, in a click reaction with at least one compound of formula (I), e.g. with C175-XX. Thereby, a variety of different labeled compounds according to formula (II) are obtained, which can be separated and analysed, preferably simultaneously, by mass spectrometry. Preferably, D-labeling and/or $^{13}C$-labeling of organic compounds according to formula (III), preferably of lipids, is useful to increase the mass of the respective compound and to shift the signal of this compound during mass spectrometry.

By using the at least one internal standard as described below according to a compound of formula (III), the different labeled compounds as described above can be quantified. Preferably, the at least one internal standard may comprise 1 or 2 or 3 alkyne groups, more preferably 1 or 2 alkyne groups, as described above, which are linked to different carbon atoms of the compound, preferably in the $R^4$ group, according to formula (III). For example, if there is more than 1 alkyne group present, the alkyne groups are linked to different fatty acids comprised in the compound, preferably in the $R^4$ group, according to formula (III). Additionally, the compounds may comprise $^{13}C$ atoms or D atoms as described above, preferably the fatty acid FA 16:2-$^{13}C9$, which is linked to an alkyne group, or the fatty acid FA 15:1-d8 are comprised in the compound of formula (III), preferably FA15:1-d8. Thereby, the signal of the internal standard can be shifted in another field of the spectra, whereby the analysis of data and the separation of signals is improved. Preferably, this method is used to separate the signals of cellular lipids and signals of the internal standards during mass spectrometry. In one preferred embodiment, alkyne-labeled and $^{13}C$-labeled cellular lipids and alkyne-labeled and D-labeled internal standards are used for click reaction and subsequent mass spectrometry.

A further aspect is a method for the detection of an organic compound, preferably a lipid, a nucleic acid, an amino acid, a peptide or a protein. This method comprises or consists of the steps:

a) reacting in a solvent at least one compound of formula (III) with at least one compound of formula (I) in the presence of catalytic amounts of Cu(I) to form a compound of formula (II), b) optionally purifying the compound of formula (II) by chromatography or liquid-liquid extraction, and c) detecting the compound of formula (II) and/or formula (IV).

The solvent can be every suitable solvent that is known to the skilled person. For example, solvents such as dimethylformamide, acetonitrile, tetrahydrofuran, dimethoxysulfoxide, dichloromethane, methanol, ethanol, 1-propanol, 2-propanol, and trimethylamine can be used. In a preferred embodiment the solvent is acetonitrile. When acetonitrile is used, the stability of Cu(I) in the solution is improved.

The compound of formula (III) is an alkyne-labeled organic compound, more preferably an alkyne-labeled lipid.

In one embodiment, the compound is derived from a lipid selected from the group consisting of saturated fatty acids, unsaturated fatty acids, glycerolipids, glycerophospholipids, lysophosphoglycerolipids, sphingolipids, sterol lipids, prenol lipids, saccharolipids, carotenoids, waxes, and polyketides.

In another embodiment, the compound is derived from a lipid selected from the group consisting of fatty acids like oleate, palmitate, and ester, amide, hydroxyl or keto derivatives thereof, sterol ester, cholesterol, cholesterol ester, cardiolipin, phosphatidylcholine, phosphatidylethanolamine, phosphatidylglycerol, phosphatidylinositol, phosphatidylserine, mono-, di-, triacylglycerol, ceramide, sphingosine and sphinganine.

In various non-limiting embodiments, the compound of formula (III), in particular $R^4$, comprises one or more D and/or one or more $^{13}C$ carbon atoms, preferably 1 or 2 or 3 or 4 or 5 or 6 or 7 or 8 or 9 or 10 or more D, preferably 8 D and/or 1 or 2 or 3 or 4 or 5 or 6 or 7 or 8 or 9 or 10 or more $^{13}C$ carbon atoms, preferably >6 $^{13}C$ carbon atoms, more preferably 8 or 9 or 10 $^{13}C$ carbon atoms, most preferably 9 $^{13}C$ carbon atoms.

Preferably, $R^4$ which is derived from an organic compound as defined above comprises either one or more D or one or more $^{13}C$ carbon atoms as defined above.

In various non-limiting embodiments, the organic compound according to formula (III) comprises 1 alkyne group (m=1). Preferably, the alkyne group is linked to one fatty acid comprised in the $R^4$ group. Typically, this fatty acid may be an even or uneven (odd), saturated or unsaturated fatty acid.

In some embodiments, this (alkyne-labeled) fatty acid may comprise 1 or 2 or 3 or 4 or 5 or 6 or 7 or 8 or 9 or 10 or more $^{13}C$ carbon atoms, preferably >6 $^{13}C$ carbon atoms, more preferably 8 or 9 or 10 $^{13}C$ carbon atoms. One non-limiting example of such a fatty acid is FA 16:2-$^{13}C9$ which can be linked to one alkyne-group.

In various non-limiting embodiments, the organic compound according to formula (III) comprises 2 alkyne groups (m=2) which are preferably linked to different carbon atoms of the $R^4$ group. Preferably, if more than one fatty acid is present in the organic compound, one alkyne group is linked to one fatty acid comprised in the $R^4$ group and the other alkyne group is linked to a second fatty acid comprised in the $R^4$ group. In this embodiment, $R^4$ is preferably derived from lipids, more preferably from di- or triacylglycerol (DAG or TAG). Typically, the comprised fatty acids may be independently selected from even or uneven, saturated or unsaturated fatty acids. In some embodiments, at least one of the fatty acids comprises 1 or 2 or 3 or 4 or 5 or 6 or 7 or 8 or 9 or 10 or more $^{13}C$ carbon atoms preferably >6 $^{13}C$ carbon atoms, more preferably 8 or 9 or 10 $^{13}C$ carbon atoms, e.g. at least one fatty acid is FA 16:2-$^{13}C9$ which is linked to one alkyne group.

In various non-limiting embodiments, the organic compound according to formula (III) comprises 1 or 2 alkyne groups as defined above. In this case, the $R^4$ group may further comprise a deuterium-labeled fatty acid, wherein this fatty acid is not linked to one of the alkyne groups. Preferably, said fatty acid comprises one or more D, more preferably 1 or 2 or 3 or 4 or 5 or 6 or 7 or 8 or 9 or 10 or more D, most preferably 8 D atoms. Preferably, the $R^4$ group is derived from a lipid, more preferably from diacylglycerol if one alkyne group is comprised in the compound of formula (III) or triacylglycerol if two alkyne groups are comprised in the compound of formula (III). For example, the deuterium labeled fatty acid comprised in the $R^4$ group is FA 15:1-d8.

In various non-limiting embodiments, the organic compound according to formula (III) comprises 3 alkyne groups (m=3) which are preferably linked to different carbon atoms of the $R^4$ group. Preferably, if more than one fatty acid is present in the organic compound, one alkyne group is linked to one fatty acid comprised in the $R^4$ group, the second alkyne group is linked to a second fatty acid comprised in the $R^4$ group and the third alkyne group is linked to a third fatty acid comprised in the $R^4$ group. In this embodiment, $R^4$ is preferably derived from triacylglycerol (TAG). Typically, these fatty acids may be independently selected from even or uneven, saturated or unsaturated fatty acids. In some embodiments, at least one of the fatty acid comprises 1 or 2 or 3 or 4 or 5 or 6 or 7 or 8 or 9 or 10 or more $^{13}C$ carbon atoms preferably >6 $^{13}C$ carbon atoms, more preferably 8 or 9 or 10 $^{13}C$ carbon atoms, e.g. at least one fatty acid is FA 16:2-$^{13}C9$ which is linked to one alkyne group.

The compound of formula (I) is preferably a trialkylammonium salt, more preferably an N-1-(4-azidobutyl)-N,N,N-trialkylammonium salt, most preferably an N-1-(4-azidobutyl)-N-ethyl-N,N-dimethylammonium salt. Further preferred, X of the compound of formula (I) is preferably selected from —H or -D, more preferably 1 to 4 X are -D and the other X are —H, or all X are H.

Additionally or alternatively, the compound, preferably in $R^1$ to $R^3$ of the compound, of formula (I) can contain one or more $^{13}C$ carbon atoms and/or one or more -D.

Additionally or alternatively, each N in the compound can independently be $^{15}N$, preferably 0, 1, 2, 3, or 4 N are independently $^{15}N$ and/or and/or each C in the compound can independently be $^{13}C$, preferably 0 or 1 $^{13}C$ are present.

In one embodiment, at least one alkyne-labeled organic compound, preferably a lipid, of formula (III) can be extracted from a cell, a tissue, an organ, a whole organism or a biological fluid, preferably from a biological fluid, e.g. blood, serum or plasma. In one embodiment, at least two alkyne-labeled organic compounds according to formula (III) are present, wherein the first compound is preferably at least one alkyne-labeled organic compound, preferably a lipid, according to formula (III) which is extracted from a cell, a tissue, an organ, a whole organism or a biological fluid, and the second compound is at least one internal standard as described below. Preferably, by using the at least one extracted compound together with the at least one internal standard in the method for the detection of an organic compound, it is possible to quantify the amount of the extracted compound.

The at least one compound of formula (III) as described above can be reacted with the compound of formula (I) to produce a compound of formula (II). Preferably, the solvent contains a Cu(I) salt or complex, more preferably, the Cu(I) salt or complex is selected from the group consisting of CuI, CuBr, CuCl, CuOTf*$C_6H_6$, [Cu(NCCH$_3$)$_4$], and Cu[acetonitrile]$_4$BF$_4$, Cu[acetonitrile]$_4$PF$_6$, and combinations thereof, most preferably the Cu(I) salt or complex is Cu(I) tetrafluoroborate.

In one embodiment, the at least one compound of formula (I) is added in excess over the compound of formula (III) to the reaction mixture. Preferably, the compound of formula (I) is added in excess over the compound of formula (III), based on the number of alkyne groups in the compound of formula (III). For example, if the compound of formula (III) comprises two alkyne groups, at least two compounds of formula (I) are added.

In one embodiment, the reaction mixture can be evaporated to increase the concentration of the at least one compound of formula (I) to a concentration range of 50-5000 μM, optionally in the range of 300-1000 μM to achieve complete reaction.

In another embodiment, the at least one compound of formula (I) is provided with a concentration range of 40-100 μM, optionally 60 μM in the reaction mixture.

In one embodiment, the at least one compound of formula (II) is extracted from a cell, a tissue, an organ, a whole organism or a biological fluid, preferably from a biological fluid, e.g. blood, serum or plasma, which has been incubated with at least one compound of formula (I) and at least one compound of formula (III), which is selected from the group consisting of glycerolipids and glycerophospholipids containing at least one terminal alkyne group, terminal alkyne cholesterol derivatives, omega alkyne oleates, omega alkyne palmitates, omega alkyne sphinganins, omega alkyne sphingosines, omega alkyne fatty acids, and omega alkyne unsaturated fatty acids.

Optionally, the formed compound of formula (II) can be purified by chromatography, e.g. by HPLC or LC, gel chromatography, Solid Phase Extraction (SPE), TLC, and SMART, preferably by HPLC or LC or Solid Phase Extraction (SPE), or by liquid-liquid extraction; preferably by liquid-liquid extraction, more preferred with chloroform/methanol/water mixtures.

If Solid Phase Extraction is used, it is preferably conducted with a reverse-phase-matrix.

Afterwards, the solvent can be removed and the compound of formula (II) can be dissolved in a new solvent, suitable for mass spectrometric measurements.

Alternatively, the reaction mixture can be evaporated to increase the concentration of the at least one compound of formula (II), preferably to a concentration range of 5-40 μM.

One suitable solvent is an alcohol/water mixture, e.g. a 2-propanol/methanol/water mixture. Additionally, ammonium salts can be added to the mixture, e.g. ammonium acetate. Every suitable solvent, which is known to the skilled person, can be applied as well.

In various non-limiting embodiments, the sample after the click reaction, preferably the compound of formula (II), can be dissolved in a solvent, suitable for mass spectrometric measurements, wherein the dissolved sample has a total volume of less than 1.5 mL, preferably less than 600 μL, more preferably 500 μL.

In various non-limiting embodiments, the sample after the click reaction, preferably the compound of formula (II), can be dissolved in a solvent, suitable for mass spectrometric measurements, wherein the dissolved sample has a total volume of less than 500 μL, more preferably less than 100 μL, more preferably less than 50 μL, most preferably 25 μL. Low volume amounts, e.g. of 25 μL, are suitable for measuring samples with only low concentrations of the compound of formula (II) by mass spectrometry. In particular, these small volume amounts are useful to study single hepatocytes by mass spectrometry.

The compound of formula (II) is preferably measured and detected by mass spectrometry, more preferably by tandem mass spectrometry. Preferably, the compound of formula (II) is exposed to a low to medium ionization energy, more preferably to an ionization energy of 10 to 50 eV, more preferably of 25 to 40 eV, most preferably of 30 to 35 eV. Thereby, the trialkylamine (neutral loss) is preferably separated from the compound of formula (II) to form the stable compound of formula (IV), which is detected by mass spectrometry.

In one embodiment, (1) at least two, preferably two to five, different compounds of formula (I) are used, wherein at least one, preferably one to four, of the compounds contain one or more substituents independently selected from -D, —F, —$^{19}$F, OH, OD, in particular -D, preferably independently present in one or more groups of $R^1$ to $R^3$, more preferably 1 to 6 -D, in particular in one or more groups of $R^1$ to $R^3$, are present Preferably, 1 to 4 -D are present in the molecule, or (2) at least two, preferably two to five, different compounds of formula (VII) are used, wherein at least one, preferably one to four, of the compounds contain one or more substituents independently selected from -D, —F, —$^{19}$F, OH, OD, in particular -D, preferably independently present in one or more groups of $R^1$ to $R^3$, more preferably 1 to 6 -D, in particular in one or more groups of $R^1$ to $R^3$, are present.

In another embodiment, (1) at least two, preferably two to four, different isotopically labeled compounds of one compound of formula (I) are used, wherein the substituent is preferably -D, more preferably wherein the substituent is present in $R^1$ to $R^3$, or (2) at least two, preferably two to four, different isotopically labeled compounds of one compound of formula (VII) are used, wherein the substituent is preferably -D, more preferably wherein the substituent is present in $R^1$ to $R^3$.

In one embodiment, if at least two compounds of formula (I) with identical total nominal mass, but different nominal mass of the trialkylammonium moiety are employed, it is possible to perform multiplexing mass spectrometry. The different nominal masses of the resulting neutral losses lead to a distinct pattern in the spectrogram. If additionally internal standards of alkyne-labeled organic compounds are employed, it is possible to quantify the targeted organic compound to be determined.

The term "nominal mass" relates to mass values that are integer of the "exact mass" (see Table 2). That means that the calculated or measured value is rounded. The rounded value is preferably used for further calculations.

Another aspect is a method for producing a compound of formula (I) according to item 1, wherein a compound according to formula (V)

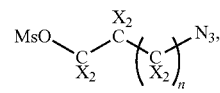

wherein X is independently selected from —H, -D, —F, —$^{19}$F, —OH, —OD;

n is 1 to 4, preferably n is 1, 2 or 3, more preferably n is 2;

Ms is a leaving group, preferably mesylate;

wherein each N in the compound can independently be $^{15}$N, preferably 0, 1, 2 or 3 N are $^{15}$N, and wherein each C in the compound can independently be $^{13}$C;

1a) is reacted with $NR^1R^2R^3$, wherein $R^1$, $R^2$ and $R^3$ are independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl, whereby the linear, branched alkyl or cycloalkyl groups can contain one or more -D and/or one or more $^{13}$C carbon atoms, or wherein $R^1$ is a free valence and $R^2$ and $R^3$ form a 4 to 7-membered cyclic hydrocarbon ring, which can contain one or more -D and/or one or more $^{13}$C carbon atoms; and wherein N can be $^{15}$N; in an organic solvent to give the compound according to formula (I)

or 1b) a compound according to formula (V) as defined above is reacted with $NR^1R^3H$, wherein $R^1$ and $R^3$ are independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl, whereby the linear, branched alkyl or cycloalkyl groups can contain one or more -D and/or one or more $^{13}$C carbon atoms, or wherein $R^1$ and R³ form a 4 to 7-membered cyclic hydrocarbon ring, which can contain one or more -D and/or one or more ¹³C carbon atoms; and wherein N can be ¹⁵N; in an organic solvent to give a compound according to formula (VI)

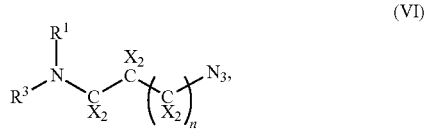

wherein X, R¹ and R³, and n are as defined above, and wherein each N can independently be ¹⁵N, preferably 0, 1, 2, 3 or 4 N are ¹⁵N; and wherein each C in the compound can independently be ¹³C; and wherein the compound of formula (VI), if R¹ and R³ are not a 4 to 7-membered cyclic hydrocarbon ring is subsequently reacted with R²Y, wherein R² is independently selected from substituted or unsubstituted linear C₁-C₁₀ alkyl, substituted or unsubstituted branched C₃-C₁₀ alkyl, substituted or unsubstituted C₃-C₁₀ cycloalkyl, whereby the linear, branched alkyl or cycloalkyl group can contain one or more -D and/or one or more ¹³C carbon atoms; and —Y is a halogen group, preferably —F, —Cl, —Br, or —I, more preferred —Br or —I, most preferred —I; to give the compound according to formula (I).

In one embodiment, route 1a) is used to provide compounds of formula (I), wherein X is preferably independently selected from —H or -D, more preferably 1 to 4 -D are present and the remaining X are —H or all X are —H. R¹, R² and R³ are independently selected from substituted or unsubstituted linear C₁-C₁₀ alkyl, substituted or unsubstituted branched C₃-C₁₀ alkyl, substituted or unsubstituted C₃-C₁₀ cycloalkyl, whereby the linear, branched alkyl or cycloalkyl groups do not contain any heavy isotopes such as one or more -D and/or one or more ¹³C carbon atoms.

In one embodiment, route 1b) is used to provide compounds of formula (I), wherein X is preferably independently selected from —H or -D, more preferably 1 to 4 -D are present and the remaining X are —H or all X are —H; and R¹, R² and R³ are independently selected from substituted or unsubstituted linear C₁-C₁₀ alkyl, substituted or unsubstituted branched C₃-C₁₀ alkyl, substituted or unsubstituted C₃-C₁₀ cycloalkyl, whereby the linear, branched alkyl or cycloalkyl groups can contain one or more -D and/or one or more ¹³C carbon atoms. Additionally, each N in the compound can independently be ¹⁵N and/or each C in the compound can independently be ¹³C.

In a final aspect, a kit for the detection of alkyne-labeled compounds may include:
i) at least one compound according to formula (I);
ii) at least one internal standard of alkyne-labeled compounds according to formula (III); and
iii) optionally at least one Cu(I) salt or complex.

In a preferred embodiment, the at least one internal standard is an internal standard mixture comprising the lipid classes CE, Cer, DAG, TAG, double-labeled TAG, PA and PC.

In another preferred embodiment, the at least one internal standard is an internal standard mixture comprising the lipid classes CE, Cer, DAG, TAG, double-labeled TAG, PA, PC, PE, PI and PS. Preferably, this internal standard mixture covers 95% of the fatty acids incorporated into cellular lipids and can be used for absolute quantification measurements.

Preferably, each lipid of CE, Cer, DAG, TAG, PA, PC, PE, PI and PS comprises one alkyne-group. The double-labeled TAG comprises two alkyne groups as described above. Additionally, each internal standard may comprise a further deuterium-labeled fatty acid as described above, e.g. FA 15:1-d8. Preferably, the alkyne-labeled fatty acid and the deuterium-labeled fatty acid are different fatty acids in the compound.

Preferably, the at least one internal standard, preferably the deuterium-labeled fatty acid, comprises 1 or 2 or 3 or 4 or 5 or 6 or 7 or 8 or 9 or 10 or more deuterium atoms (D), more preferably 8 D, e.g. the fatty acid FA 15:1-d8.

In various embodiments it is possible, but not preferred, that the at least one internal standard according to formula (III) further comprises 1 or 2 or 3 or 4 or 5 or 6 or 7 or 8 or 9 or 10 or more ¹³C carbon atoms preferably >6 ¹³C carbon atoms, more preferably 8 or 9 or 10 ¹³C carbon atoms, e.g. at least one fatty acid is FA 16:2-¹³C9 which is linked to one alkyne group.

In preferred embodiments, alkyne-labeled and D-labeled internal standards are useful to differentiate the at least one internal standard or mixture thereof from cellular compounds, preferably cellular lipids, wherein the cellular lipids are alkyne-labeled and/or ¹³C-labeled. Another embodiment to differentiate cellular lipids and lipids of the internal standard mixture is the use of even alkyne-labeled fatty acids for internal standard compounds and uneven alkyne-labeled fatty acids, which are added to the test system, preferably to the cell, tissue, organ, whole organism or biological fluid, more preferably to the cell, tissue or whole organism. By using these combinations, it is possible to separate the masses of cellular lipids from masses of internal standard compounds during mass spectrometry. Preferably, this makes it possible to add more than one fatty acid to the test system, preferably to the cell, and to detect the products simultaneously, afterwards.

All items and embodiments described herein in the context of the compounds are also applicable in the described uses, methods and kit; and vice versa.

BRIEF DESCRIPTION OF THE DRAWINGS

The accompanying drawings serve to afford an understanding of various embodiments. The drawings illustrate embodiments and together with the description serve to elucidate same. Further embodiments and numerous advantages from among those intended are evident directly from the following detailed description. The elements and structures shown in the drawings are not necessarily illustrated in a manner true to scale with respect to one another.

DETAILED DESCRIPTION

Examples

Chemical Synthesis

Figure 1:
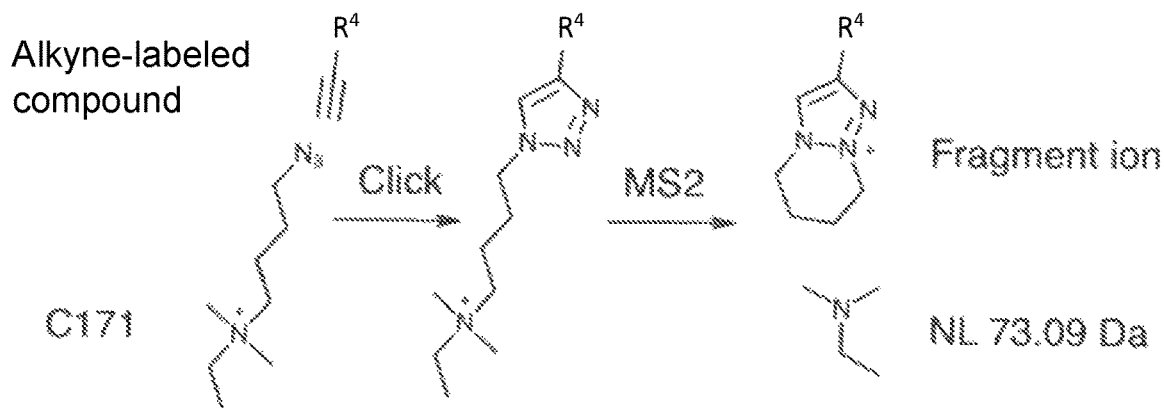
FIG. 1 Detection of alkyne-labeled compounds by click reaction with trialkylammonium salts (here C171) and subsequent mass spectrometry, whereby a stable cyclic fragment ion and a neutral trialkylamine group are formed and measured.
Figure 2:
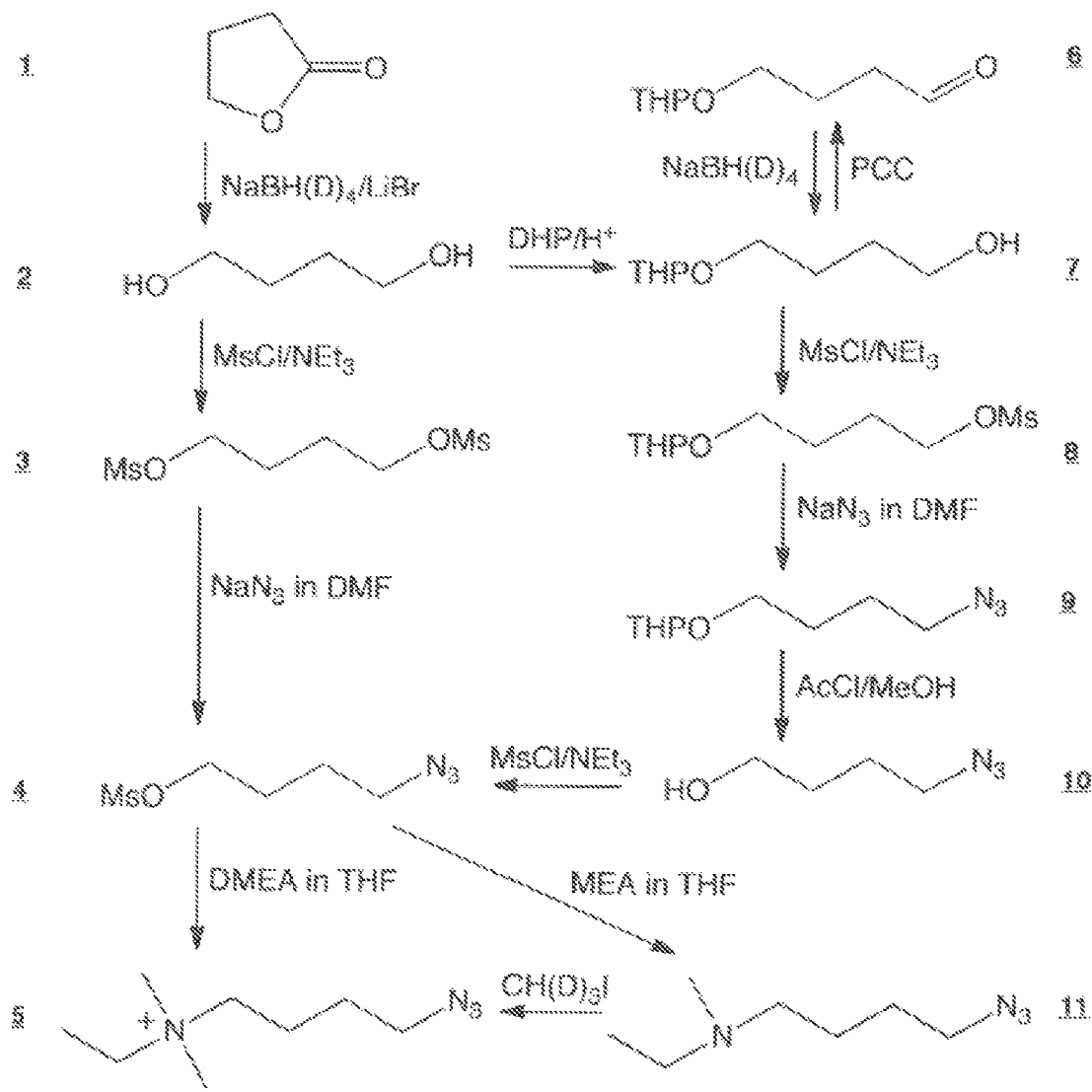
FIG. 2 Chemical synthesis strategies to provide compounds of formula (I). The following abbreviations have been used: Ms=mesylate, DMF=dimethylformamide, PCC=pyridinium chlorochromate, THP=tetrahydropyran, AcCl=acetyl chloride, DMEA=N,N-dimethyl-N-ethylamine, MEA=N-methyl-N-ethylamine, DHP=dihydropyran, and THF=tetrahydrofuran.

The strategy for synthesis of C171 (N-1-(4-azidobutyl)-N-ethyl-N-dimethylammonium salt) and the C175-XX series is depicted in FIG. 2. There are two different synthesis routes. The first started with commercially available butyrolactone 1, butanediol 2, or its bis-methansulfonate 3. It was reacted with sodium azide to the azidobutylmesylate 4. The second route started with mono-tetrahydropyran (THP) butanediol 7 (Petroski, Synth. Commun., 2006, 33, 18, 3251-3259) or the THP-protected semialdehyde 6 (Petroski, Synth. Commun., 2006, 33, 18, 3251-3259). After activation to the mesylate 8 and reaction with sodium azide the protective group was removed to obtain 4-azido-1-butanol 10. Upon activation with MsCl, the routes converge at the azidobutylmethansulfonate 4. Depending on the needs, 4 was directly reacted with dimethylethylamine to give the trialkylammonium product 5, or sequentially reacted with methylethylamine to intermediate 11, followed by methylation with methyl iodide to give product 5. The latter reaction serves to introduce heavy isotopes into the alkylammonium head group, whereas two reductions with complex borodeuteride (1→2, 6→7) were used to introduce deuterium atoms into the butanediol moiety (see FIG. 2). d4-Butanediol can be obtained commercially.

Example 1: Synthesis of C171

4-Azidobutan-1-ol (10): To a stirred solution of 20 mmol (3.48 g) mono-THP butanediol 7 and 3.0 g (30 mmol) trimethylamine in 100 mL $CH_2Cl_2$ was added at 0° C. to a solution of 22 mmol (2.52 g) methanesulfonylchloride in 8 mL $CH_2Cl_2$. After 2 h of stirring, the reaction was quenched with 10 mL 5% citric acid in water. The aqueous layer was removed, the organic phase washed with water and brine, dried over sodium sulfate and evaporated to obtain 4.7 g of the mono-THP mesylate 8 as a viscous liquid that was used without further purification. Four gram of 8 were stirred for 16 h at 60° C. with a solution of 3 g (46 mmol) $NaN_3$ in 30 mL DMF. After addition of 50 mL ethyl acetate and 50 mL hexane, the mixture was extracted with 2×30 mL water and 50 mL brine, dried over sodium sulfate and the solvent was removed to give 3 g (14 mmol) of protected azidobutanol 9. Thin layer chromatography (TLC) analysis (hexane/ethyl acetate 1/1) showed complete conversion with two minor impurities. For removal of the THP-group, the material was dissolved in 100 mL methanol plus 0.6 mL acetyl chloride. After 5 min, the solvent was removed in vacuo and the residue purified on silica column (hexane/ethyl acetate 1/1) to obtain 1.4 g (12.2 mmol) product. NMR (400 MHz in $CDCl_3$): 1.7 ppm (m, 4H, 2,3-$CH_2$), 3.34 ppm (t, J=6.5 Hz, 2H, 4-$CH_2$), 3.70 ppm (t, J=6.1 Hz, 2H, 1-$CH_2$).

4-Azido-1-(methylsulfonyloxy)butane (4): Alcohol 10 (1.4 g) was reacted with 1.8 g triethylamine and 1.6 g methanesulfonyl chloride in 60 mL $CH_2Cl_2$ to obtain 2.2 g of 4. NMR (400 MHz in $CDCl_3$): 1.74 ppm (m, 2H, 3-$CH_2$), 1.87 ppm (m, 2H, 2-$CH_2$), 3.04 ppm (s, 3H, S—$CH_3$), 3.38 ppm (t, J=6.6 Hz, 2H, 4-$CH_2$), 4.28 ppm (t, J=6.1 Hz, 2H, 1-$CH_2$).

At this point, the mesylate 4 was either directly reacted with N-ethyl-N,N-dimethylamine to give the non-isotope labeled reagent C171 (same strategy as used for the synthesis of C175-73) or was reacted with N-ethyl-N-methylamine to give nor-methyl-C171. This was used to introduce isotope labels into the alkylammonium group by reaction with accordingly labeled methyl iodide (i.e. the synthesis of C175-75, -76, and -77).

Example 2: N-Ethyl-N-methyl-1-(4-azidobutyl)amine (11), nor-methyl-C171)

A solution of 100 µL (140 mg, 0.7 mmol) 4 and 200 µL (140 mg, 2.4 mmol) N-ethyl-N-methylamine in 0.5 mL THF was heated in a closed tube under argon for 6 h at 60° C. The solvent was removed in a stream of argon. The residue was dissolved in 3 mL $CH_2Cl_2$, the solution was extracted with 1 mL 1 M NaOH and washed with 2 mL water. The organic phase was collected, dried over sodium sulfate and evaporated to give 11 (100 mg, 0.6 mmol), which can be used for further synthesis without purification (see FIG. 2). NMR (400 MHz in $CDCl_3$): 1.07 ppm (t, J=7.2 Hz, 3H, ethyl-$CH_3$), 1.60 ppm (m, 4H, 2,3-$CH_2$), 2.23 ppm (s, 3H, methyl-$CH_3$), 2.38 ppm (t, J=7.3 Hz, 2H, ethyl-$CH_2$, 1-$CH_2$), 2.44 ppm (q, J=7.2 Hz, 2H, ethyl-$CH_2$), 3.45 ppm (t, J=6.6 Hz, 2H, 4-$CH_2$).

Example 3: C171

A solution of 400 µL (560 mg, 2.9 mmol) 4 and 400 µL (270 mg, 3.7 mmol) N-ethyl-N,N-dimethylamine in 1 mL CH$_2$Cl$_2$ was heated in a closed tube under argon for 6 h at 60° C. TLC control showed complete conversion. The solvent was removed in a stream of argon and the residue precipitated and washed with ether (3×6 mL) and hexane (2×6 mL). The solvent was removed in vacuo to give C171 (570 mg, 2.15 mmol) as its mesylate salt.

NMR (400 MHz in CDCl$_3$): 1.38 ppm (t, J=7.3 Hz, 3H, ethyl-CH$_3$), 1.67 ppm (m, 2H, 3-CH$_2$), 1.83 ppm (m, 2H, 2-CH$_2$), 2.69 ppm (s, 3H, S—CH$_3$), 3.21 ppm (s, 6H, methyl-CH$_3$), 3.45 ppm (m, 6H, ethyl-CH$_2$, 1-CH$_2$, 4-CH$_2$), 3.45 ppm (m, 2H+q, 4H, J=7.3 Hz, 1-CH$_2$+ethyl-CH$_2$).

Subsequently, the mesylate was exchanged against the BF$_4^-$-anion. C171-mesylate salt (570 mg) was dissolved in 10 mL 50% MeOH. The solution was loaded on a 5 mL column of Amberlite A26 (purchased in the OH$^-$-form, washed sequentially with 8 vol. each of 50% MeOH, 1 M NaOH, water, 1 M NH$_4$BF$_4$, water, 50% MeOH) and eluted with 50% MeOH. The first 1.5 mL flow-through were discarded and the following 20 mL pooled to obtain a 100 mM solution of C171-BF$_4$ that was used for click reactions.

Example 4: C175-73

1 g (10.6 mmol), 2,3-d4-butanediol (Cambridge Isotopes) was reacted with two equivalents of methanesulfonylchloride as described above to give d4-1,4-bis(methylsulfonyloxy)butane in quantitative yield. To minimize risk from handling this potentially dangerous compound, the entire amount was dissolved in 30 mL DMF and stirred with 825 mg (1.2 eq.) NaN$_3$ for 16 h at 60° C. After standard workup (see above), 2,3-d4-4 was isolated by chromatography on silica gel (hexane/ethyl acetate 2/1) to give 700 mg product. Reaction with dimethylethylamine (see C171) yielded 760 mg C175-73 as the mesylate salt (see FIG. 2).

Example 5: C175-75

Sodiumborodeuteride (1 g, 24 mmol) and 2.06 g (24 mmol) LiBr were dissolved in 20 mL THF and stirred for 20 min at 65° C. Gammabutyrolactone (2 mL, 26 mmol) were added and stirring continued at 60° C. under argon for 16 h. Then 300 µL CH$_3$OD and 1 mL D$_2$O were added subsequently and stirring was continued for 5 min, followed by addition of 20% HCl until the mixture was acidic. The upper, organic phase was collected, the lower phase extracted with 2×5 mL THF and the combined THF phases evaporated, which resulted in a viscous liquid and large amounts of solid, presumably boric acid and related compounds. The entire material was loaded onto a short silica column and extracted with CHCl$_3$/MeOH/H$_2$O 30/60/10. The solvent was removed to obtain 2 g of viscous, impure material. For further purification, the butanediol was converted to its mono-THP ether according to the procedure of Petroski (Petroski, Synth. Commun., 2006, 33, 18, 3251 to 3259) and added 2 mL 0.1 M HCl and 25 mmol dihydropyran in 60 mL DCM, followed by stirring for 96 h. The mixture was neutralized with saturated NaHCO$_3$, the CH$_2$Cl$_2$ phase was collected, dried and the solvent evaporated. The residue was purified on silica gel with hexane/ethyl acetate 1/1 to obtain 710 mg d2-7 mono-THP ether along with 1 g of the di-protected diol. The d2-7 was converted to d2-4 as outlined above to give 3.5 mmol (680 mg) product, which was reacted with a 3-fold excess of ethylmethylamine in 2 mL THF for 6 h at 60° C. After addition of 10 mL water and 15 mL 1M NaOH, the mixture was extracted with 3×30 mL CH$_2$Cl$_2$, the extracts were combined and the solvent removed in vacuo. The residue was dissolved in 2 ml THF and treated with 5 mmol (700 mg, 313 µL) CHD$_2$I (Sigma-Aldrich) in 2 mL THF. After 1 h of stirring at 50° C., ether (5 mL) was added, the upper phase discarded and the lower phase washed with ether and hexane to give C175-75 as the iodide salt (see FIG. 2).

Example 6: C175-76

A solution of 210 mg (5.1 mmol) NaBD$_4$ in 15 mL 0.1 N NaOH in D$_2$O was added in one batch to a stirred solution of 2.5 g (14.5 mmol) 6 in 35 mL THF. After 5 min, TLC control showed complete conversion to the alcohol. Brine (10 mL) was added, the THF phase collected and the water phase re-extracted with 10 mL ethyl acetate. Organic phases were combined, washed with brine, dried and evaporated. The residue was purified on silica (hexane/ethyl acetate/trimethylamine, 50/50/1) to give 2.0 g (11.4 mmol) 4-d1-7. After activation with MsCl (2 g 7, 1.43 g MsCl, 1.7 g triethylamine, 50 mL CH$_2$Cl$_2$, to give 2.88 g 4-d1-8), subsequent reaction with sodium azide (2.3 g in 30 mL DMF to give 2.24 g 4-d1-9), removal of THP, activation with MsCl (1.35 g 4-d1-9, 1.7 g ethylmethylamine in 3 mL THF at 60 for 3 h to yield 1.53 g 4-d1-11. This was reacted with a 3-fold excess of CD$_3$I in THE to give 2.5 g of C175-76 as the iodide salt (see FIG. 2).

Example 7: C175-77

To prepare $^{13}$CD$_3$I from $^{13}$CD$_3$OH, the procedure of Olah et al. (Olah et al. Angew. Chem. Int. Ed. Engl., 1979, 18, 612 to 614) was used. To a stirred solution of $^{13}$CD$_3$OH (128 mg, 4 mmol) and sodium iodide (600 mg, 4 mmol) in 4 mL dry acetonitrile was slowly added 500 µL (430 mg, 4 mmol) chlorotrimethylsilane. After 30 min of stirring, the tube was centrifuged for 5 min at 500 g and the supernatant was transferred into a tube that contained a solution of 470 mg (3 mmol) of 11 in 1 mL THF. The mixture was stirred for 4 h at room temperature. The major part of the solvent was evaporated in a stream of argon to leave about 1.5 mL, the product was precipitated as its iodide salt by addition of 6 mL ether and the precipitate washed with ether (3×6 mL) to give 750 mg of C175-77 as an iodide salt (see FIG. 2).

Purification for all C175 reagents: The raw material (600-1500 mg) was dissolved in 10 mL 50% MeOH and passed over a column of 5 mL Amberlyst A15 (purchased in the H$^+$-form, washed with 10 vol. 50% MeOH, 10 vol. 1 M NH$_3$ in H$_2$O, 10 vol. 1 M ammonium formate in 50% MeOH and 10 vol. 50% MeOH). The column was washed with 50% MeOH until absorbance of 280 nm and conductivity returned to the baseline. The product was eluted with 40 mL 1 M ammonium formate in 50% MeOH. The eluates were evaporated at a final vacuum of 1.5 mbar at 70° C. until all remnants of ammonium formate had disappeared, leaving the formate salts of the reagents as viscous liquids. These formates were analyzed by 1H-NMR:

C175-73: (400 MHz in CDCl$_3$): 1.40 ppm (t, J=7.3 Hz, 3H, ethyl-CH$_3$), 3.17 ppm (s, 6H, methyl-CH$_3$), 3.42 ppm (2×s, 4H, 1-CH$_2$, 4-CH$_2$), 3.48 ppm (q, J=7.3 Hz, 2H, ethyl-CH$_2$).

C175-75: (400 MHz in CDCl$_3$): 1.41 ppm (t, J=7.3 Hz, 3H, ethyl-CH$_3$), 1.67 ppm (m, 2H, 3-CH$_2$), 1.84 ppm (m, 2H, 2-CH$_2$), 3.14 ppm (s, 1H, methyl-CD$_2$H), 3.17 ppm (d, J=1.0 Hz, 3H, methyl-CH$_3$), 3.46 ppm (m, 4H, ethyl-CH$_2$, 1-CH$_2$, 4-CH$_2$).

C175-76: (400 MHz in CDCl$_3$): 1.41 ppm (t, J=7.3 Hz, 3H, ethyl-CH$_3$), 1.67 ppm (m, 2H, 3-CH$_2$), 1.84 ppm (m, 2H, 2-CH$_2$), 3.17 ppm (s, 3H, methyl-CH$_3$), 3.45 ppm (m, 5H, ethyl-CH$_2$, 1-CH$_2$, 4-CH$_2$).

C175-77: (400 MHz in CDCl$_3$): 1.40 ppm (t, J=7.3 Hz, 3H, ethyl-CH$_3$), 1.67 ppm (m, 2H, 3-CH$_2$), 1.84 ppm (m, 2H, 2-CH$_2$), 3.20 ppm (d, J=3.6 Hz (couples to $^{13}$C of the $^{13}$CD$_3$-methyl), 3H, methyl-CH$_3$), 3.45 ppm (m, 6H, ethyl-CH$_2$, 1-CH$_2$, 4-CH$_2$).

Anion exchange: For use of the C175 reagents in the click reaction, the formate was exchanged against the BF$_4^-$-anion. This was done to avoid possible interference of the formate with the Cu(I)-ions in the click reaction and possible adduct formation in MS. Since the Cu(I) is supplied as the BF$_4^-$-salt anyway, the formate was exchanged against BF$_4^-$. Each reagent (220 mg, 1 mmol) was dissolved in 3 mL 50% MeOH. The solution was loaded on a 5 mL column of Amberlite A26 (purchased in the OH$^-$-form, washed sequentially with 8 vol. each of 50% MeOH, 1 M NaOH, water, 1 M NH$_4$BF$_4$, water, 50% MeOH) and eluted with 50% MeOH. The first 1.5 mL flow-through were discarded and the following 10 mL pooled to obtain 100 mM solutions of C175-XX$^+$BF$_4^-$, which were used for subsequent click reactions.

For MS analysis of isotopic purity, the reagents were diluted to 10 μL in MeOH and analyzed in MS1 and MS2. First, isotopic composition was examined and it was found that all reagents showed a major peak at the expected nominal mass m/z 175 plus the expected first isotope peak at m/z 176 with about 8% intensity relative to the monoisotopic peak. In addition, peaks at m/z 174 were found, indicating incomplete replacement of hydrogen by deuterium, with relative intensities ranging between 1.5% (C175-77) and 6.5% (C175-75). Subsequently, all 12 isotope peaks were analyzed in MS2 to determine the distribution of isotopes between the dimethylethylamino group and the butanediol moiety. The C175 reagents show a uniform fragmentation with neutral loss of nitrogen plus the dimethylethylamine group, leaving the cation of the butanediol-N, likely in a cyclic form. From the pattern of these ions, the isotope composition of each of the C175 reagents was calculated in detail. For all the C175-XX reagents, the fraction of the monoisotopic peak with the correct NL of the alkylamine group is between 86 and 91%. In the first isotope peaks at m/z 176, both NL of XX and of XX+1 were found, indicating that the $^{13}$C, which gives rise to the m/z 176 peaks, distributes as expected over both the butanediol and the alkylamine moiety. In contrast, for the peaks of m/z 174 the defect (missing deuterium) was found to localize mostly to the butanediol moiety, with the exception of C175-77, which has an unlabeled butanediol and therefore a small deuterium defect in the alkylamine group. These data enable correction of the primary NL mass spectra for the specific properties of each of the four reagents.

Quantitative Internal Standards

Alkyne-labeled standards were synthesized in a 10-50 mg scale using standard lipid synthesis techniques. All compounds were purified using silica gel chromatography, dissolved at 1 mg/mL in methanol (PC, PA) or 2-propanol and mixed to obtain a standard mix stock solution, which subsequently was calibrated against two unlabeled quantitative standard mixtures.

TABLE 1

Alkyne-labeled standards, their synthesis method and their calculated and measured masses (m/z).

| Standard name | Synthesis | Calculated and measured masses (m/z) |
|---|---|---|
| PC(16:0/a18:3) | Acylation of LPC (16:0) using EDC/DMAP | [M + H]$^+$ meas: 756.551, calc: 756.554 |
| PA(a17:2/17:1) | Acylation of sn-glycerol-3 diethylphosphate and subsequent deprotection with bromotrimethylsilane (Gaebler et al., J. Lipid Res., 2013, 54, 8, 2282-2290) | [M + H]$^+$ meas: 669.451, calc: 669.450 |
| Cer(d18:1/a18:3) | Acylation of sphingosine with a 18:3-NHS | [M + H]$^+$ meas: 560.502, calc: 560.504 |
| TG(14:0/17:1/a17:2) | Acylation of DG (14:0/17:1) using EDC/DMAP | [M + NH$_4$]$^+$ meas: 818.721, calc: 818.723 |
| CE(a18:3) | Acylation of cholesterol using EDC/DMAP | [M + NH$_4$]$^+$ meas: 664.602, calc: 664.603 |
| DG(a17:2/15:0) | Acylation of MG(a17:2) using EDC/DMAP | [M + NH$_4$]$^+$ meas: 582.508, calc: 582.509 |
| TG(a17:2/15:0/a19:3) | Acylation of DG(a17:2/15:0) using EDC/DMAP | [M + NH$_4$]$^+$ meas: 856.735, calc: 856.739 |

Example 8: Multiplexing

Figure 7A:
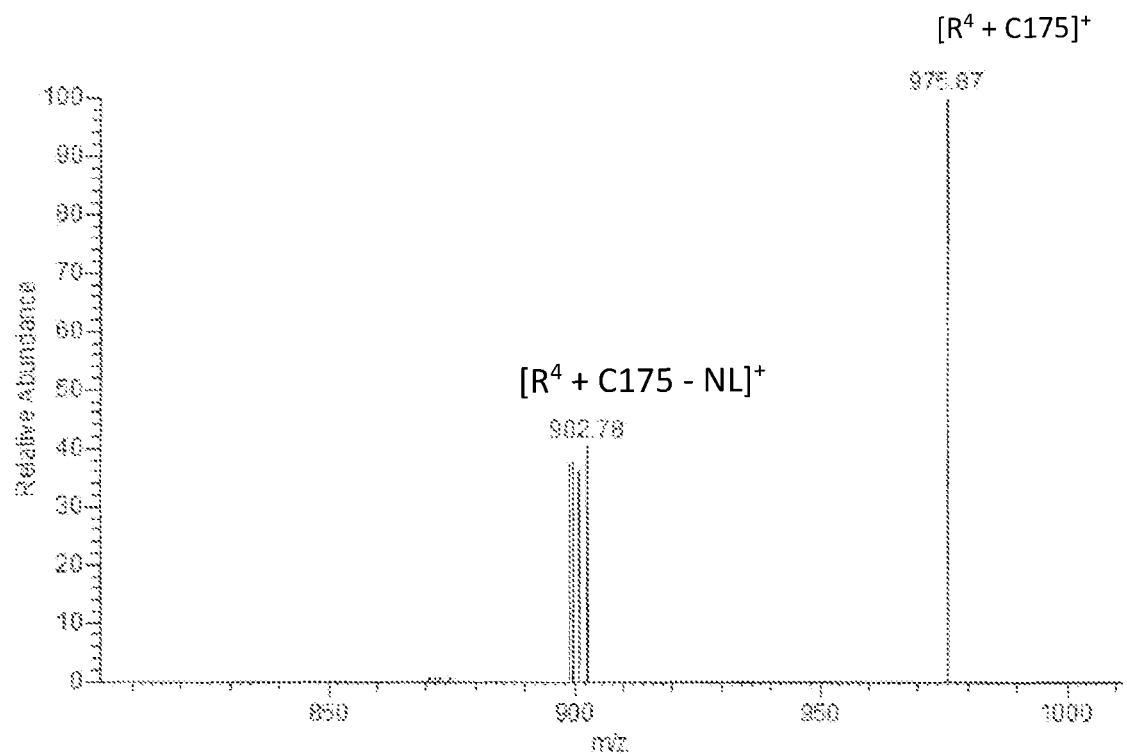
FIG. 7 Multiplexed analysis of alkyne-labeled lipids in hepatocytes: Mouse hepatocytes were grown in single wells of a multiwall plate for 2 h in the presence of alkyne-palmitate and in the absence or presence of different inhibitors of DGAT1 or DGAT2, or a combination thereof. Cells were washed to remove the alkyne-palmitate and lipids were extracted by $CHCl_3$/MeOH along with addition of a mixture of various internal standards. Lipid extracts were reacted with C175-73, -75, -76, or -77. Afterwards, the samples reacted with different C175-XX reagents were pooled and analyzed together by tandem mass spectrometry. 7A) MS2 spectrum at the mass of the internal standard for triacylglycerol TG(48:3), demonstrating the equal amount and response in the four samples. 7B) MS2 spectrum at the mass of triacylglycerol TG(49:4), which was synthesized by the cells, demonstrating the different effects of DGAT inhibitors on the amount of this TG in the sample.
Figure 7B:
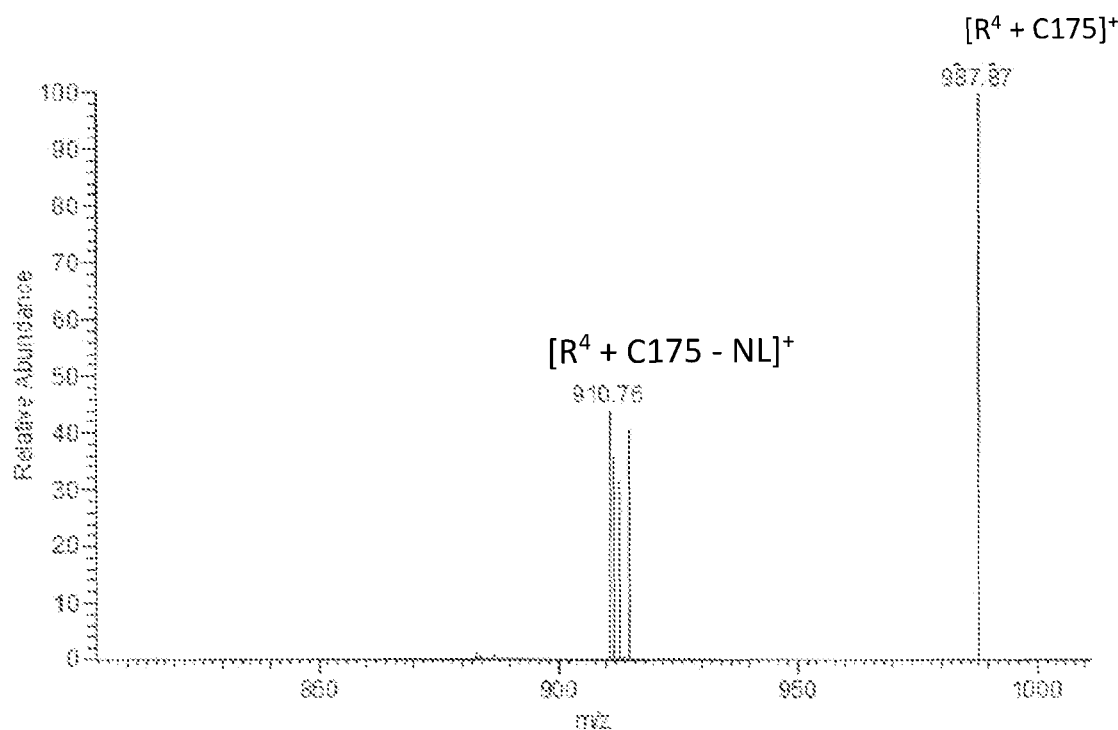
Figure 8A:
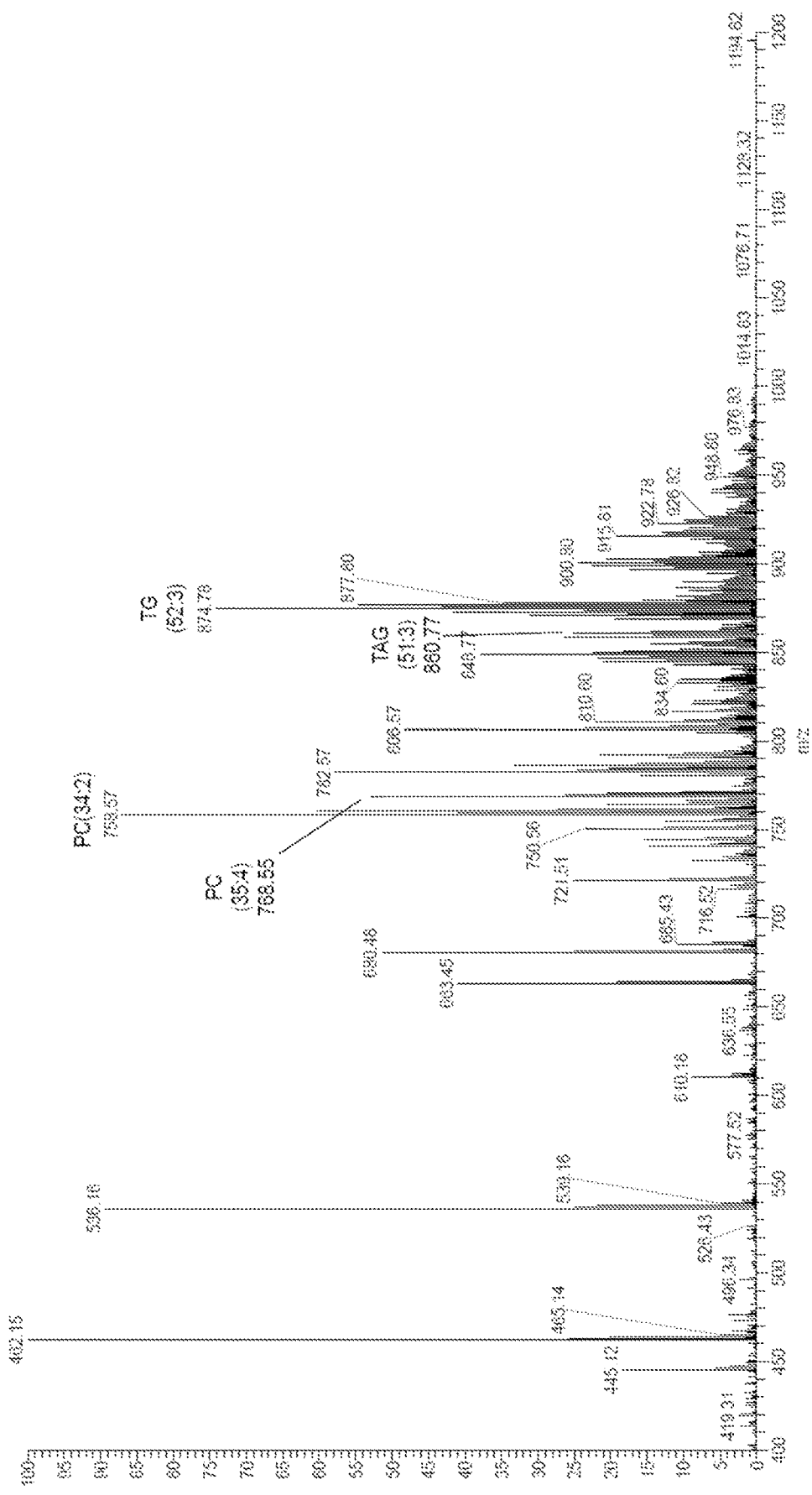
FIG. 8A Complete mass spectrum of hepatocytes grown for 2 h with alkyne-palmitate before click reaction.

Multiplexed analysis of alkyne-labeled lipids in hepatocytes was performed. Mouse hepatocytes were grown in single wells of a multiwall plate for 2 h in the presence of alkyne-palmitate and in the absence or presence of different inhibitors of DGAT1 or DGAT2, or a combination thereof. Cells were washed to remove the alkyne-palmitate and lipids were extracted by CHCl$_3$/MeOH along with addition of a mixture of various internal standards. Lipid extracts were reacted with C175-73, -75, -76, or -77. Afterwards, the samples reacted with different C175-XX reagents were pooled and analyzed together by tandem mass spectrometry. FIG. 7A shows a MS2 spectrum at the mass of the internal standard for triacylglycerol TG(48:3), demonstrating the equal amount and response in the four samples. FIG. 7B shows a MS2 spectrum at the mass of triacylglycerol TG(49:4), which was synthesized by the cells, demonstrating the different effects of DGAT inhibitors on the amount of this TG in the sample. The complete mass spectrum of hepatocytes grown for 2 h with alkyne-palmitate before and after click reaction are shown in FIGS. 8A (before) and 8B (after).

Advantages Over Known Analysis Methods

The compounds and methods and uses associated therewith, have many advantages over known analysis methods:

The reaction of the alkyne-labeled compound of formula (III) with the click reagent of formula (I) results in a mass increase of the resulting molecule of formula (II). For example, in case of C171, the click reagent has a mass of 171.16 Da. During mass spectrometry, the mass of the measured compound shifted by 171 Da. Thereby, labeled lipids can be shifted in a nearly empty field of the spectra, whereby the analysis of data and the separation of signals is improved (see FIG. 8A/8B).

Because of the four nitrogen atoms in the compound according to formula (II), the compound identification in mass spectra is improved.

Fragmentation of compounds of formula (II) during mass spectrometry is surprisingly uniform. Using low to medium ionization energies, no fragmentation of the triazol ring of formula (II) occurs. Only a neutral loss of the trialkylammonium group takes place. It is assumed, without being bound to any theory, that the compound of formula (II) forms a stable cyclic product of formula (IV) after separation of the trialkylammonium group.

Figure 3:
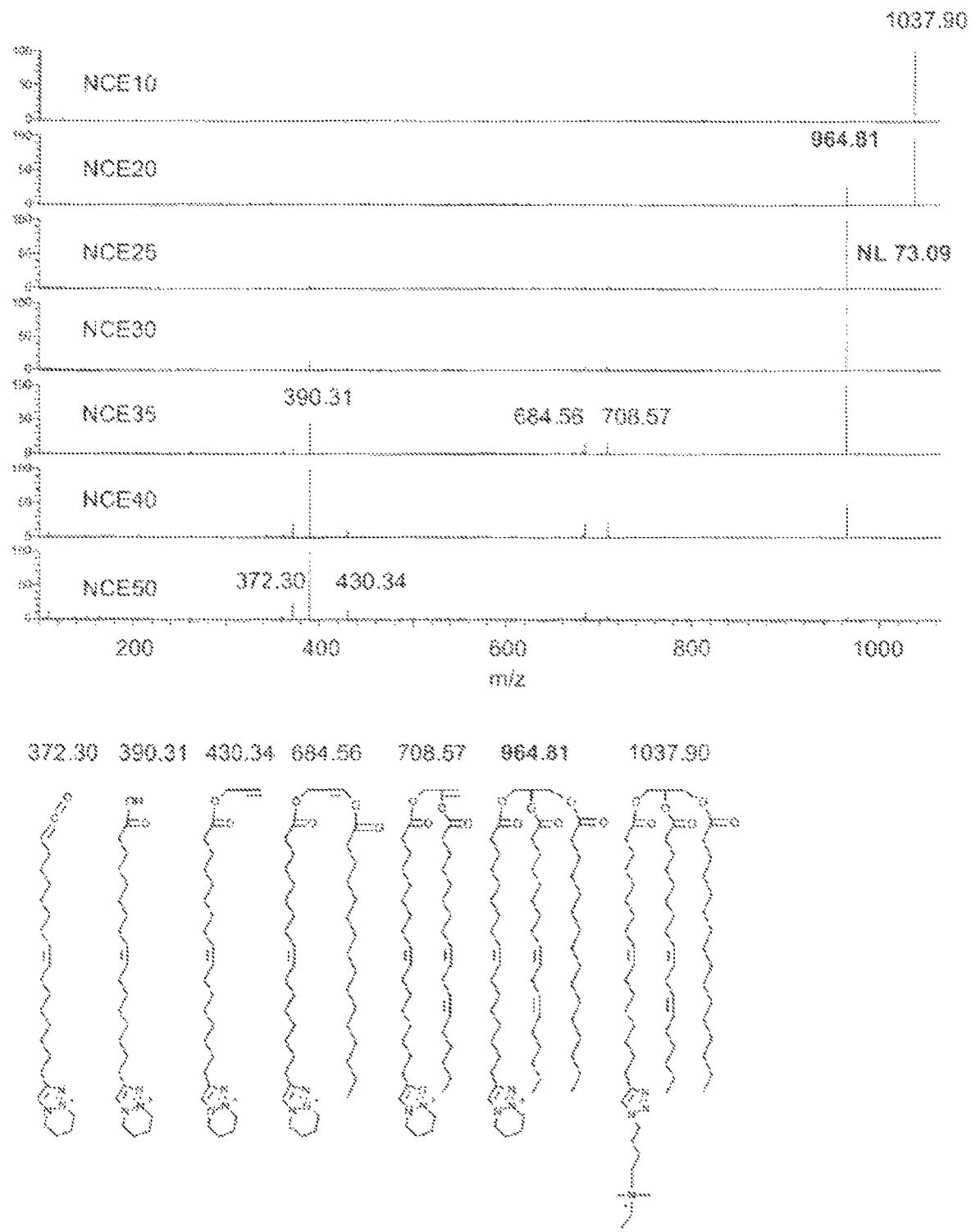
FIG. 3 General degradation pattern of measured neutral lipids (mono-, di-, triacylglycerols, sterol ester, ceramides), simple fatty acids and derivatives thereof (ester, amide, hydroxyl or keto fatty acids) after click reaction with C171 und subsequent mass spectrometry at ionization energies of 30 to 35 eV.

Preferably, with ionization energies of 10 to 50 eV, more preferably of 25 to 40 eV, most preferably of 30 to 35 eV, the neutral loss is the only fragmentation of compounds of formula (II) and the fragmentation is nearly complete. With higher ionization energies, further fragmentations can take place, but preferably, a degradation of the triazol ring does not occur (see fragmentation pattern of FIGS. 3 and 4). With too low ionization energies, the fragmentation can be incomplete and not consistent.

Figure 4:
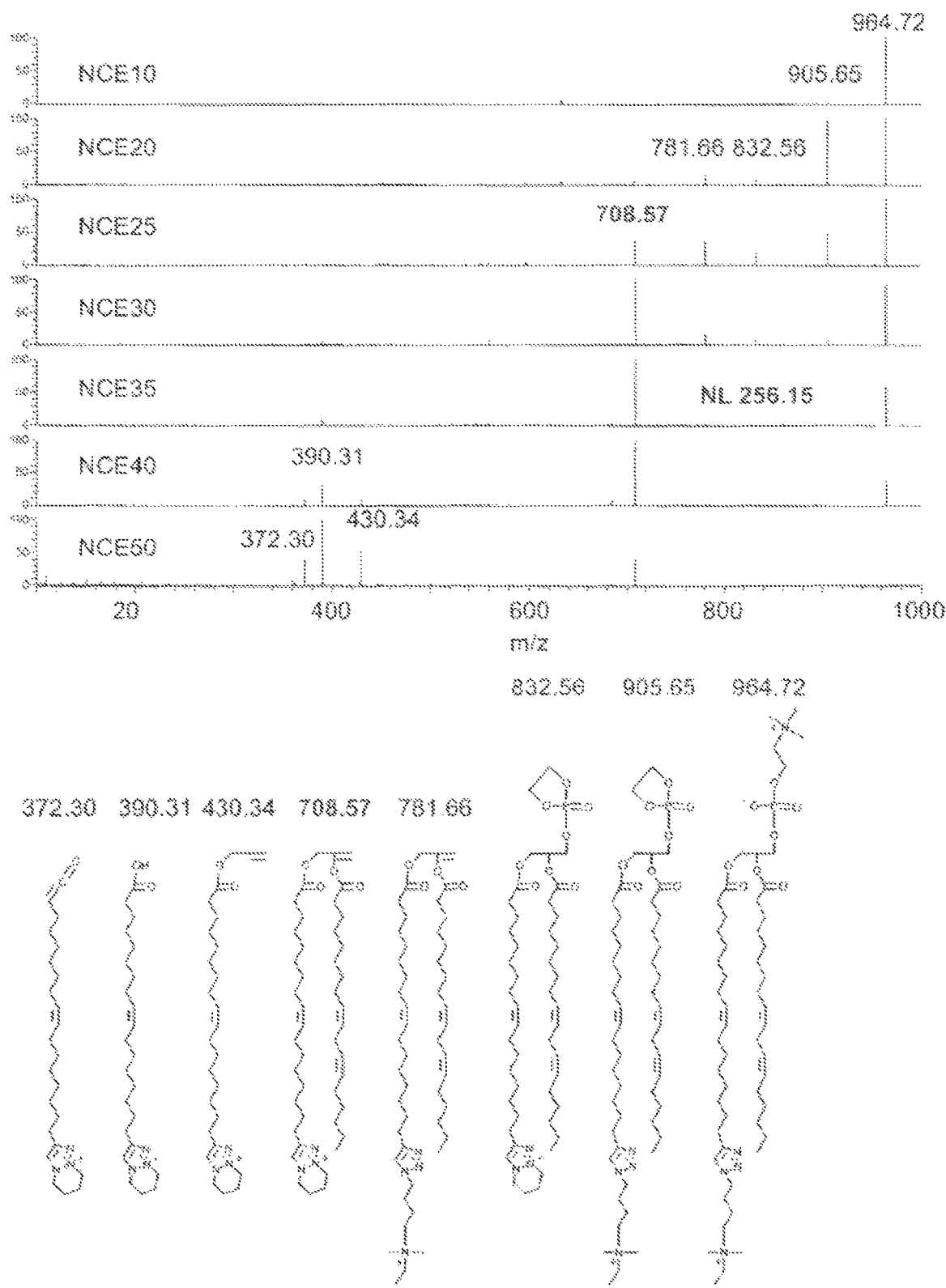
FIG. 4 Degradation pattern of phosphatidylcholine after click reaction with C171 and subsequent mass spectrometry by ionization energies of 30 to 35 eV. The head group and the trialkylammonium group are both eliminated uniformly as neutral losses (neutral loss of head group+73.09 Da (trialkylamine)).

With phosphatidylcholine, the head group and the trialkylammonium group are both eliminated uniformly as neutral losses (neutral loss of head group+73.09 Da) with ionization energies of 30 to 35 eV (see FIG. 4). Based on the neutral loss, the corresponding phosphatidylcholine can be identified. If C171 would set free a charged reporter ion, the identification and differentiation in MS/MS would not be possible.

Figure 8B:
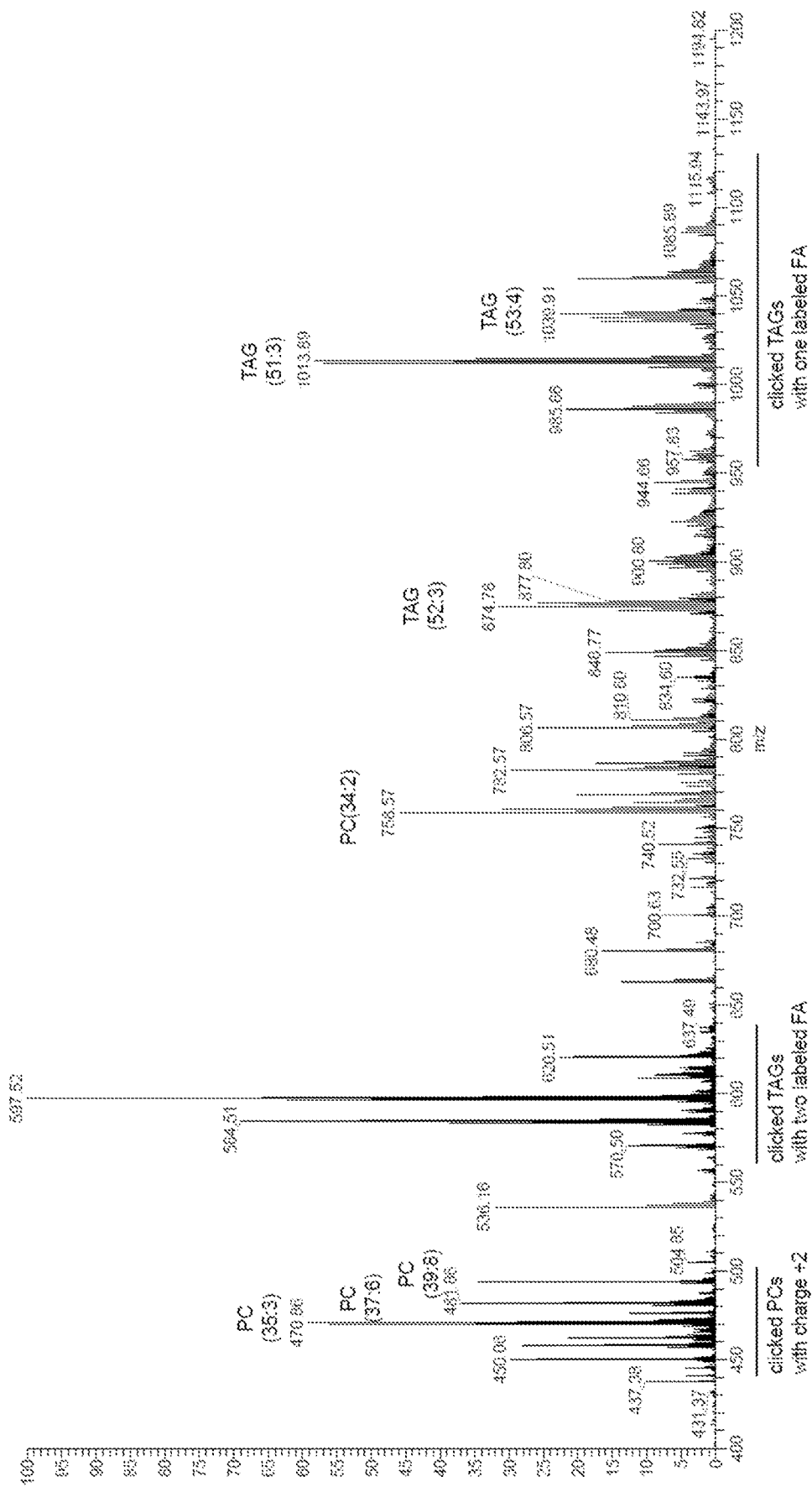
FIG. 8B Complete mass spectrum of hepatocytes grown for 2 h with alkyne-palmitate after click reaction.

The permanent positive charge of the compound of formula (II) leads to an improved ionization and signal strength of measured lipids (see FIG. 8B).

Typical Procedure for Utilizing C171:

1) Metabolic labeling of the usually living biological test system with an alkyne-labeled precursor, e.g. a fatty acid. Alternatively, all known alkyne-labeled compounds can be used such as lipids, nucleic acids, amino acids, peptides or proteins.

2) Finishing the labeling and subsequent extraction of the labeled metabolites, optionally addition of alkyne-labeled internal standard lipids for a later absolute quantification.

3) Click reaction with C171 in the presence of Cu(I), preferably in an organic solvent containing Cu(I)-tetrafluoroborate.

4) For lipids: Removal of reagents by chloroform/methanol/water 2-phase-distribution. Lipids are present the chloroform phase, ionic compounds are present the water/methanol phase.

5) Drying of the chloroform phase and dissolving the residue in a suitable organic solvent mixture for use in mass spectrometry, preferably isopropanol/methanol/water mixtures with addition of ammonium acetate are used.

6) MS and MS/MS analysis: The preferred form of analysis of lipids is a so-called shotgun-analysis of the unseparated mixture by direct infusion into the mass spectrometer (e.g. commercially available Thermo Q-Exactive Plus with a HESI ion source). The lipid sample was sprayed into the mass spectrometer by a standard syringe pump for 10 to 30 min with 2 to 10 µL/min. In this time, MS1 spectra (generally 300-1200 Da) and subsequently MS/MS spectra were measured program-controlled over the whole range (steps of 1 Da, selection window of 1 Da, charge +1) and subsequently MS/MS spectra of 300 to 700 Da were measured (steps 0.5 Da, selection window 0.7 Da, charge +2). The measured data set contains MS1 and MS/MS data for each positive ion of the selected measuring range, which enables the later broad evaluation of each lipid class 7) For evaluation of the measurements, the software LipidXplorer (3) was used, which is platform independent and available free of charge. With this software, it is possible to define search parameters in so-called MFQL files, which work with a molecular search logic, with which the data set can be searched.

MFQL files can be set up for every lipid class. Phosphatidylcholine and triacylglycerol give, in addition to the usual signals with charge of +1, also signals with charge of +2. In case of phosphatidylcholine, these signals occur because of the stable charge of the head group. In case of triacylglycerol, it occurs because of the introduction of two labeled fatty acids in the triacylglycerol molecule. These species can be detected and quantified by corresponding MFQL files, if corresponding spectra were measured during data acquisition. Reading and searching of a data set of 10 samples with usual search parameters and 20 MFQL files needs approximately 20 minutes and detects 150 to 500 labeled species, when labeled with 16-heptadecynoic acid, also called "Click-Palmitate".

Absolute quantification of lipid amounts in a sample is possible, using internal standards. Preferably, a mixture of synthetic internal standards, which are alkyne-labeled lipids of known concentrations with unnatural fatty acid patterns, can be added to the sample, preferably during lipid extraction. Intensities of the samples can be compared to intensities of the internal standards to calculate the present concentrations. The usual internal standard mixture contains the most important lipid classes (MAG, DAG, TAG, Cer, CE, PA, PC). The extension of the mixture by new developed and synthesized standards is possible. In one embodiment, the internal standard mixture contains lipid classes CE, Cer, (MAG), DAG, TAG, double-labeled TAG, PA, PC, PE, PI and PS.

The lower detection limit for most of the lipid classes is at approximately 0.02 pmol per species in the complete sample, which is a low concentration in comparison to other methods, especially unlabeled analysis methods. The reduction of the sample concentration is possible due to the improved ionization of the permanent charge of C171.

Figure 5:
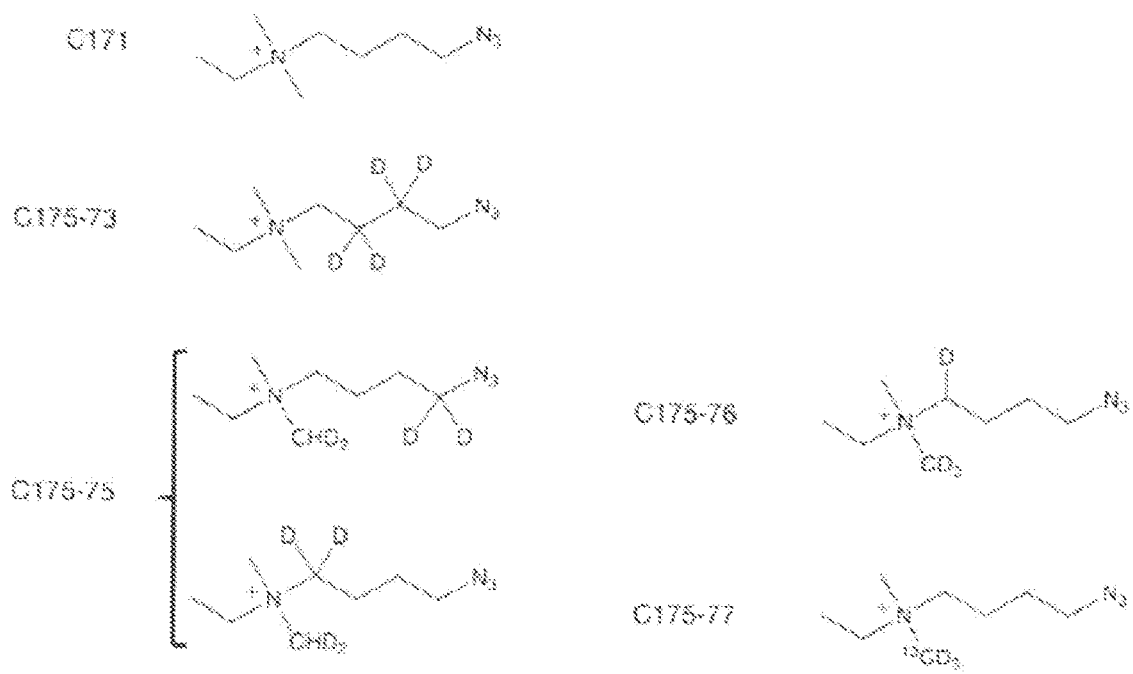
FIG. 5 Preferred compounds according to formula (I) (click reagents C171 and C175-XX).

Multiplex-Analysis: C171 has a flexible basic structure, which allows the formation of different variants. Heavy isotopes (-D, $-^{13}C$, $-^{15}N$) can be integrated in parts of the molecule, whereby the same nominal mass, but different neutral losses occur (see Table 2). Labeled lipid samples, which are clicked with different reagents (for example variants C175-XX, see FIG. 5), can be pooled and analyzed in combination. Thereby, experimental noise due to variations in sample handling, spray fluctuations, ionization suppression or fluctuations in fragmentation is reduced. Furthermore, the comparability of samples is improved and the measurement time reduced.

Figure 6:
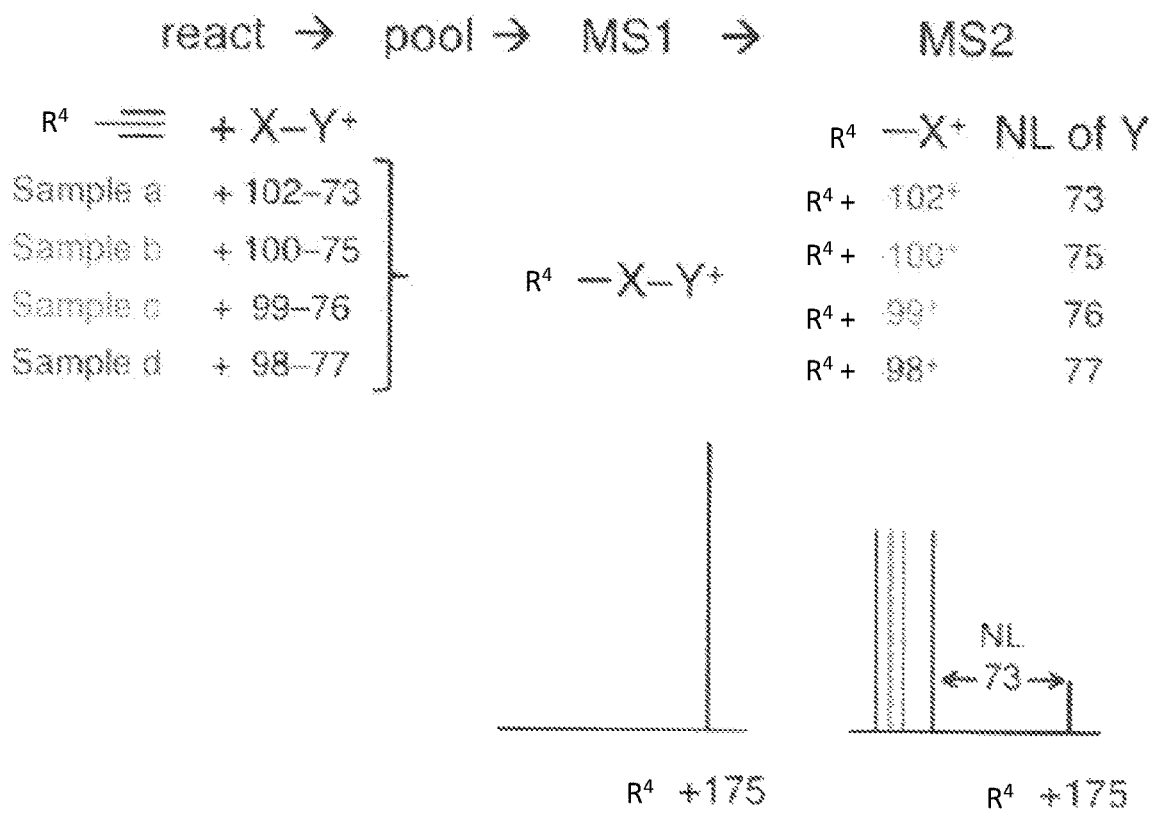
FIG. 6 Mass distribution of samples a) to d), after click reaction with different compounds of formula (I) and subsequent detection by mass spectrometry, showing the general concept of multiplexing.

The difference of the C175-XX procedure and the procedure with C171 is that the four samples of C175-XX are pooled after click reaction (see FIG. 6).

C175-77 and C175-73 to 76 differ in their mass by 2.87 mDa. This difference is not recognized by MS1, whereby only one peak is present (see FIG. 6). Only in MS2, after neutral loss of the C175-reagents, the single peak is separated into four peaks, which contain information about the amount of precursors in the single samples (see FIG. 6).

After syntheses of C175 reagents, the content of monoisotopic reagent is in the range of 87 to 91%. 9 to 13% are different impurities, which result from $^{13}C$ content and incomplete substitution with -D. As a result, multiplex peaks have complex disorders in the range of 3 to 5% of intensity. Since this disorder occurs in all samples uniformly, the error can be eliminated by relative standardization.

By utilization of an internal standard, the error can be corrected and total quantification is possible.

TABLE 2

Overview of preferred compounds (C171 and C175-XX) according to formula (I) and their corresponding masses before and after fragmentation (neutral loss) by mass spectrometry.

| | | | | Nominal mass | Exact mass | NL mass | Remaining mass |
|---|---|---|---|---|---|---|---|
| $C_4H_{11}$ | N | $C_4H_8$ | $N_3$ | 171 | 171.16097 | 73.08915 | 98.07182 |
| $C_4H_{11}$ | N | $C_4H_4D_4$ | $N_3$ | 175 | 175.18553 | 73.08915 | 102.09693 |
| $C_4H_9D_2$ | N | $C_4H_6D_2$ | $N_3$ | 175 | 175.18553 | 75.10170 | 100.08438 |
| $C_4H_8D_3$ | N | $C_4H_7D_1$ | $N_3$ | 175 | 175.18553 | 76.10798 | 99.07810 |
| $C_3{}^{13}C_1H_8D_3$ | N | $C_4H_8$ | $N_3$ | 175 | 175.18260 | 77.11133 | 98.07182 |

TABLE 3

Neural loss of click reagents (C171, C175-XX) bound to different labeled lipid samples (PA, PC, PE, PG, PI, PS, MAG, DAG, TAG, Cer, free fatty acids).

| | NL of head group | NL after click reaction with | | | | |
|---|---|---|---|---|---|---|
| | | C171 | C175-73 | C175-75 | C175-76 | C175-77 |
| PA | 97.977 | 171.066 | 171.066 | 173.079 | 174.085 | 175.088 |
| PC | 183.066 | 256.155 | 256.155 | 258.168 | 259.174 | 260.177 |
| PE | 141.019 | 214.108 | 214.108 | 216.121 | 217.127 | 218.130 |
| PG | 172.014 | 245.103 | 245.103 | 247.116 | 248.122 | 249.125 |
| PI | 260.030 | 333.119 | 333.119 | 335.132 | 336.138 | 337.141 |
| PS | 185.009 | 258.098 | 258.098 | 260.111 | 261.117 | 262.120 |
| MAG, DAG, TAG, Cer, free fatty acids | 0 | 73.089 | 73.089 | 75.102 | 76.108 | 77.111 |

Evaluation of Data

1. The intensities of the four peaks can be compared to each other, whereby relative amounts can be calculated.

2. If internal standards are added to the samples during lipid extraction, total amounts of the sample precursors can be calculated.

Quantitative Alkyne-Labeled and Deuterium-Labeled Internal Standards

TABLE 4

Alkyne-labeled and deuterium-labeled standards, their synthesis method and their calculated and measured masses (m/z).

| Standard name | Synthesis | Calculated and measured masses (m/z) |
|---|---|---|
| PA(a17:2-15:1-d8) | Sequential acylation of sn-glycerol-3 diethylphosphate with alkyne-palmitate (aPal) and FA15:1-d8 and subsequent deprotection with bromotrimethylsilane (see Gaebler et al., J. Lipid Res. 54, 2281-2290 (2013)) | $[M + NH_4]^-$ meas: 668.510 calc: 668.510 |
| PC(a17:2-15:1-d8) | Reaction of PA(a17:2-15:1-d8) with choline tosylate in pyridine/trichloroacetonitrile | $[M + H]^+$ meas: 736.571 calc: 736.573 |
| PE(a17:2-15:1-d8) | PLD-catalyzed reaction of PC(a17:2-15:1-d8) with ethanolamine (see Gaebler et al., J. Lipid Res. 54, 2281-2290 (2013)) | $[M + H]^+$ meas: 694.525 calc: 694.526 |
| PS(a17:2-15:1-d8) | Reaction of PA(a17:2-15:1-d8) with Boc-Ser(OH)-tBu in pyridine/trichloroacetonitrile and subsequent deprotection in TFA/DCM | $[M + H]^+$ meas: 738.513 calc: 738.5155 |

TABLE 4-continued

Alkyne-labeled and deuterium-labeled standards, their synthesis method and their calculated and measured masses (m/z).

| Standard name | Synthesis | Calculated and measured masses (m/z) |
|---|---|---|
| PI(a17:2-15:1-d8) | Sequential acylation of glycerol-phospho-(2,3:4,5-dicyclohexylidene-6O-methoxymethyl-inositol, see Aneja, U.S. Pat. No. 7,977,497B2 (2011)) followed by deprotection using bromotrimethylsilane in DCM. | $[M + NH_4]^+$ meas: 830.561 calc: 830.563 |
| dhCer (alkyne-d18:2/15:1-d8) | Acylation of alkyne-sphinganine (Gaebler et al., J. Lipid Res. 54, 2281-2290 (2013) with FA15:21-d8-NHS | $[M + H]^+$ meas: 528.523 calc: 528.523 |
| DAG (a17:2/15:1-d8) | Acylation of MG(a17:2) with FA15:1-d8 using EDC/DMAP | $[M + NH_4]^+$ meas: 588.543 calc: 588.544 |
| TAG (a17:2/15:1-d8/16:0) | Acylation of DG(a17:2/15:1-d8) with palmitic acid using EDC/DMAP | $[M + NH_4]^+$ meas: 826.774 calc: 826.773 |
| TAG (a17:2/15:1-d8/a17:2) | Acylation of DG(a17:2/15:1-d8) with aPal using EDC/DM AP | $[M + NH_4]^+$ meas: 826.774 calc: 826.773 |
| CE (a17:2-d7) | Acylation of commercial cholesterol-d7 with aPal using EDC/DMAP | $[M + NH_4]^+$ meas: 659.647 calc: 659.647 |

Exemplary Synthesis of Deuterium-Labeled Fatty Acids:
Pentadec-11c-enoic Acid (12,13,14,15-D8, FA15:1-D8)

D10-Butanol (2 g) and 5 g powdered molecular sieve was treated with 2 equivalents of pyridinium chlorochromate in 100 ml dichloromethane to give d8-butanal that was isolated by distillation. 1-tetrahydropyranyl-oxy-undecanyl-triphenylphosphonium bromide was reacted with one equivalent of lithiumhexamethylenedisilazane in THF and the resulting Wittig reagent reacted with the d8-butanal to give THP-protected pentadec-11c-en-1-ol (12,13,14,15-D8). The THP group was removed by treatment with HCl in dry methanol and the free alcohol was oxidized with $H_2SO_4/CrO_3$ in acetone to give the final product.

The invention claimed is:

1. A compound comprising formula (I)

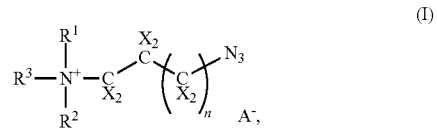

(I)

wherein $R^1$ to $R^3$ are independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl, wherein the linear, branched alkyl, or cycloalkyl groups can contain one or more -D atoms, one or more $^{13}C$ carbon atoms, or combinations thereof; or wherein $R^1$ is a free valence, and $R^2$ and $R^3$ form a 4 to 7-membered cyclic hydrocarbon ring, wherein the 4 to 7-membered cyclic hydrocarbon ring can contain one or more -D atoms, one or more $^{13}C$ carbon atoms, or combinations thereof; or wherein $R^1$ and $R^2$ are each methyl and $R^3$ is ethyl;
wherein n is 2;
wherein 1 to 4 X are -D and the remaining X are —H;

wherein A⁻ is an anion;
wherein each N in the compound can independently be $^{15}$N; and wherein each C in the compound can independently be $^{13}$C; and
wherein if $R^1$ to $R^3$ are substituted, the substituent is independently selected from -D, —F, —$^{19}$F, —OH, or —OD.

2. A compound comprising formula (II)

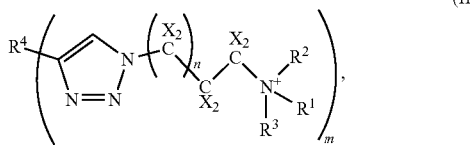

wherein $R^1$ to $R^3$ are independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl; wherein the linear, branched alkyl, or cycloalkyl groups can contain one or more -D atoms, one or more $^{13}$C carbon atoms, or combinations thereof, and wherein if $R^1$ to $R^3$ are substituted the substituent is independently selected from -D, —F, —$^{19}$F, —OH, or —OD; or
wherein $R^1$ is a free valence, and $R^2$ and $R^3$ form a 4 to 7-membered cyclic hydrocarbon ring, wherein the 4 to 7-membered cyclic hydrocarbon ring can contain one or more -D atoms, one or more $^{13}$C carbon atoms, or combinations thereof;
wherein n is 2;
wherein 1 to 4X are -D and the remaining X are —H;
wherein m ranges from 1 to 3; wherein each N in the compound can independently be $^{15}$N; and wherein each C in the compound can independently be $^{13}$C;
wherein the compound of formula (II) is obtained by reacting a compound of formula (I) according to claim 1 with an organic compound of formula (III)

wherein $R^4$ is derived from an organic compound; and wherein m ranges from 1 to 3.

3. A compound of formula (IV)

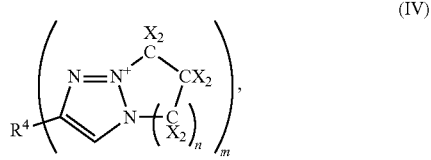

wherein $R^4$ is derived from an organic compound;
wherein 1 to 4X are -D and the remaining X are —H;
wherein m ranges from 1 to 3;
wherein n ranges from 1 to 4;
wherein each N in the compound can independently be $^{15}$N; and
wherein each C in the compound can independently be $^{13}$C;

wherein the compound of formula (IV) is obtained by treating a compound of formula (II) according to claim 2 in a mass spectrometer.

4. A method for the detection of an organic compound, wherein the method comprises:
reacting in a solvent at least one compound of formula (III) with at least one compound of formula (I) as defined in claim 1; wherein the reaction occurs in the presence of catalytic amounts of Cu(I) to form a compound of formula (II);
optionally purifying the compound of formula (II) by chromatography or liquid-liquid extraction; and
detecting the compound of formula (II), formula (IV), or combinations thereof;
wherein formula (III) comprises:

wherein $R^4$ is derived from an organic compound, and wherein m ranges from 1 to 3;
wherein formula (II) comprises:

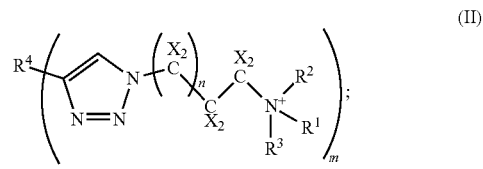

wherein $R^1$ to $R^3$, X, A−, N, and C are defined the same as $R^1$ to $R^3$, X, A−, N, and C of formula (I) in claim 1;
wherein formula (IV) comprises:

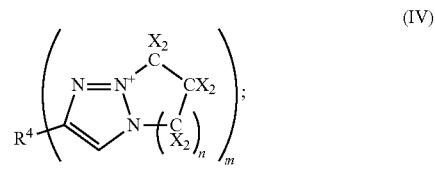

wherein R4 is derived from an organic compound; and wherein X, A−, N, and C are defined the same as X, A−, N, and C of formula (I) in claim 1.

5. The method according to claim 4, wherein
the at least one compound of formula (I) is provided in excess over the at least one compound of formula (III); and wherein the method further comprises evaporating the solvent to concentrate the reaction mixture and aid in complete reaction of the at least one compound of formula (I) with the at least one compound of formula (III) to form the compound of formula (II).

6. The method of claim 4, wherein one or more of the following occurs:
the at least one compound of formula (III) is derived from a lipid selected from the group consisting of saturated fatty acids, unsaturated fatty acids, glycerolipids, glycerophospholipids, lysophosphoglycerolipids, sphingolipids, sterol lipids, prenol lipids, saccharolipids, carotenoids, waxes, and polyketides;
the method further comprises adding a Cu(I) salt or complex to the reaction mixture;

the method further comprises adding a Cu(I) salt or complex, wherein the Cu(I) salt or complex is selected from the group consisting of CuI, CuBr, CuCl, CuOTf*C$_6$H$_6$, [Cu(NCCH$_3$)$_4$], and Cu[acetonitrile]$_4$BF$_4$, Cu[acetonitrile]$_4$PF$_6$, and combinations thereof;

the method further comprises evaporating the solvent of the reaction mixture to increase the concentration of the at least one compound of formula (II);

the method further comprises evaporating the solvent of the reaction mixture to increase the concentration of the at least one compound of formula (I) to a concentration from 50 to 5000 µM;

the method further comprises providing the at least one compound of formula (I) at a concentration range from 40 to 100 µM;

the chromatography is selected from the group consisting of HPLC, LC, gel chromatography, Solid Phase Extraction (SPE), TLC, SMART, and combinations thereof;

the liquid-liquid extraction is performed with a mixture of CHCl$_3$/MeOH/H$_2$O;

further comprising drying the compound obtained after the liquid-liquid extraction and dissolving the residue in isopropanol/methanol/H$_2$O comprising ammonium acetate;

the detection occurs by mass spectrometry;

wherein the method further comprises extracting the at least one compound of formula (III) from a cell, a tissue, an organ, a whole organism, or a biological fluid prior to reacting the at least one compound of formula (III) with the at least one compound of formula (I).

7. The method according to claim 4, wherein one or more of the following occurs:

the compound of formula (III) is derived from a lipid selected from the group consisting of oleate, palmitate, cholesterol, cholesterol ester, cardiolipin, phosphatidylcholine, phosphatidylethanolamine, phosphatidylglycerol, phosphatidylinositol, phosphatidylserine, mono-, di-, and triacylglycerol, sphingosine and sphinganine;

the method further comprises extracting the at least one compound of formula (III) from a cell, a tissue, an organ, a whole organism or a biological fluid reacting the at least one compound of formula (III) with the at least one compound of formula (I);

the method further comprises extracting the at least one compound of formula (II) from a cell, a tissue, an organ, a whole organism, or a biological fluid prior to reacting the at least one compound of formula (III) with the at least one compound of formula (I); wherein the cell, the tissue, the organ, the whole organism, or the biological fluid has been incubated with at least one compound of formula (I) and at least one compound of formula (III), wherein the at least one compound of formula (III) is derived from a compound selected from the group consisting of glycerolipids and glycerophospholipids containing at least one terminal alkyne group, terminal alkyne cholesterol derivatives, omega alkyne oleates, omega alkyne palmitates, omega alkyne sphinganins, omega alkyne sphingosines, omega alkyne fatty acids, and omega alkyne unsaturated fatty acids.

8. The method according to claim 4, wherein at least two different compounds of formula (I) are included in the reaction mixture, wherein at least one of the compounds of formula (I) comprises one or more substituents independently selected from -D, —F, —$^{19}$F, OH, OD, and combinations thereof; or at least two different compounds of formula (VII) are used,

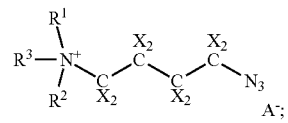

(VII)

wherein at least one of the compounds of formula (VII) comprises one or more substituents independently selected from -D, —F, —$^{19}$F, OH, OD, and combinations thereof.

9. The method according to claim 4, wherein at least two different isotopically labeled compounds are present in the reaction mixture; wherein one of the at least two different isotopically labeled compounds is a compound of formula (I); or at least two different isotopically labeled compounds are present in the reaction mixture;

wherein one of the at least two different isotopically labeled compounds is a compound comprising formula (VII):

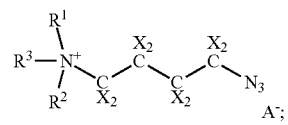

(VII)

wherein:

R$^1$ to R$^3$, X, A–, N, and C are defined the same as R$^1$ to R$^3$, X, A–, N, and C of formula (I) in claim 1.

10. A method for producing a compound of formula (I) according to claim 1; wherein:

a compound according to formula (V) is reacted with NR$^1$R$^2$R$^3$ in an organic solvent to give the compound according to formula (I);

wherein the compound of formula (V) comprises:

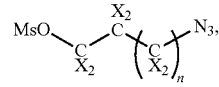

(V)

wherein X is independently selected from —H, -D, —F, —$^{19}$F, —OH, —OD;

n ranges from 1 to 4;

Ms is a leaving group;

wherein each N is $^{15}$N, and wherein each C is $^{13}$C;

wherein R$^1$, R$^2$, and R$^3$ are independently selected from substituted or unsubstituted linear C$_1$-C$_{10}$ alkyl, substituted or unsubstituted branched C$_3$-C$_{10}$ alkyl, substituted or unsubstituted C$_3$-C$_{10}$ cycloalkyl; wherein the linear, branched alkyl, or cycloalkyl groups comprise one or more -D atoms, one or more $^{13}$C carbon atoms, or combinations thereof; or wherein R$^1$ is a free valence and R$^2$ and R$^3$ form a 4 to 7-membered cyclic hydrocarbon ring, wherein the 4 to 7-membered cyclic hydrocarbon ring comprises one or more -D atoms, one or more $^{13}$C carbon atoms, or combinations thereof; and wherein N is $^{15}$N;

or a compound according to formula (V) is reacted with NR$^1$R$^3$H in an organic solvent to give a compound according to formula (VI), wherein R[1] and R[3] are independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl; wherein the linear, branched alkyl, or cycloalkyl groups comprise one or more -D atoms, one or more $^{13}C$ carbon atoms, or combinations thereof; or wherein R[1] and R[3] form a 4 to 7-membered cyclic hydrocarbon ring, wherein the 4 to 7-membered cyclic hydrocarbon ring comprises one or more -D atoms, one or more $^{13}C$ carbon atoms, or combinations thereof; and wherein N is $^{15}N$;

wherein formula (VI) comprises:

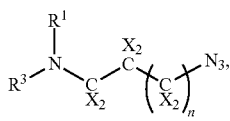

(VI)

wherein X, R[1] and R[3], and n are as defined above, and wherein each N is optionally $^{15}N$; and wherein each C is optionally $^{13}C$; and wherein the compound of formula (VI), if R[1] and R[3] are not a 4 to 7-membered cyclic hydrocarbon ring is subsequently reacted with R[2]Y, wherein R[2] is independently selected from substituted or unsubstituted linear $C_1$-$C_{10}$ alkyl, substituted or unsubstituted branched $C_3$-$C_{10}$ alkyl, substituted or unsubstituted $C_3$-$C_{10}$ cycloalkyl; wherein the linear, branched alkyl, or cycloalkyl group comprises one or more -D atoms, one or more $^{13}C$ carbon atoms, or combinations thereof; and —Y is a halogen group.

11. A kit for the detection of alkyne-labeled compounds comprising or consisting of:
at least one compound according to formula (I) of claim 1;
at least one internal standard of alkyne-labeled compounds according to formula (III);
wherein formula (III) comprises:

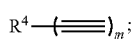

(III)

wherein R4 is derived from an organic compound, and wherein m ranges from 1 to 3; and
optionally at least one Cu(I) salt or complex.

12. A compound comprising formula (I)

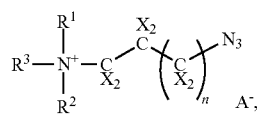

(I)

wherein R[1] and R[2] are each methyl and R[3] is ethyl;
wherein n is 2;

wherein each X is independently selected from —H, -D, —F, —$^{19}F$, —OH, —OD;
wherein A⁻ is an anion; and
wherein each N in the compound can independently be $^{15}N$; and wherein each C in the compound can independently be $^{13}C$.

13. A method for producing a compound of formula (I) according to claim 12, wherein:
a compound according to formula (V) is reacted with NR[1]R[2]R[3] in an organic solvent to give the compound according to formula (I);
wherein the compound of formula (V) comprises:

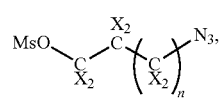

(V)

wherein X is independently selected from —H, -D, —F, —$^{19}F$, —OH, —OD;
wherein n is 2;
Ms is a leaving group;
wherein each N is $^{15}N$, and/or wherein each C is $^{13}C$;
wherein R[1] and R[2] are each methyl and R[3] is ethyl and can contain one or more -D atoms, one or more $^{13}C$ carbon atoms, or combinations thereof; and wherein N is $^{15}N$;

or a compound according to formula (V) is reacted with NR[1]R[3]H in an organic solvent to give a compound according to formula (VI), wherein
R[1] is methyl and R[3] is ethyl and can contain one or more -D atoms, one or more $^{13}C$ carbon atoms or a combination thereof; and wherein N is $^{15}N$
wherein formula (VI) comprises:

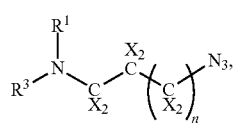

(VI)

wherein X, R[1] and R[3], and n are as defined above, and wherein each N is optionally $^{15}N$; and wherein each C is optionally $^{13}C$; and wherein the compound of formula (VI), is subsequently reacted with R[2]Y,
wherein R[2] is independently selected from substituted or unsubstituted methyl and can contain one or more -D atoms and a $^{13}C$ carbon atoms or a combination thereof; and
—Y is a halogen group.

14. The compound of formula (II) according to claim 2, wherein each N is $^{15}N$, and/or wherein each C is $^{13}C$.

15. The compound of formula (IV) according to claim 3, wherein each N is $^{15}N$, and/or wherein each C is $^{13}C$.

16. A compound comprising formula (II)

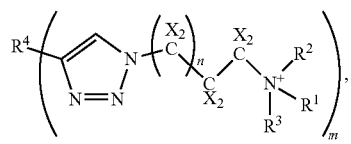

(II)

wherein $R^1$ and $R^2$ are each methyl and $R^3$ is ethyl and can contain one or more -D atoms, one or more $^{13}C$ carbon atoms, or combinations thereof, and wherein if $R^1$ to $R^3$ are substituted the substituent is independently selected from -D, —F, —$^{19}$F, —OH, or —OD;

wherein n is 2;

wherein each X is independently selected from —H, -D, —F, —$^{19}$F, —OH, —OD;

wherein m ranges from 1 to 3; wherein each N in the compound can independently be $^{15}$N;

and wherein each C in the compound can independently be $^{13}$C;

wherein the compound of formula (II) is obtained by reacting a compound of formula (I) according to claim 12 with an organic compound of formula (III)

$$R^4\!-\!\!\!(\!\!\equiv\!\!)_m; \qquad (III)$$

wherein $R^4$ is derived from an organic compound; and wherein m ranges from 1 to 3.

\* \* \* \* \*